US 8,853,167 B2

(12) United States Patent
Kato et al.

(10) Patent No.: US 8,853,167 B2
(45) Date of Patent: Oct. 7, 2014

(54) SHORT-CHAIN CATIONIC POLYAMINO ACID AND USE THEREOF

(75) Inventors: Yasuki Kato, Kashiwa (JP); Atsushi Ishii, Kashiwa (JP); Naoya Shibata, Kashiwa (JP); Tatsuyuki Hayashi, Kashiwa (JP); Kazunori Kataoka, Tokyo (JP); Kanjiro Miyata, Tokyo (JP); Nobuhiro Nishiyama, Tokyo (JP)

(73) Assignee: NanoCarrier Co., Ltd., Kashiwa-Shi (JP)

( * ) Notice: Subject to any disclaimer, the term of this patent is extended or adjusted under 35 U.S.C. 154(b) by 328 days.

(21) Appl. No.: 13/258,663

(22) PCT Filed: Feb. 23, 2011

(86) PCT No.: PCT/JP2011/053917
§ 371 (c)(1),
(2), (4) Date: Sep. 22, 2011

(87) PCT Pub. No.: WO2011/105402
PCT Pub. Date: Sep. 1, 2011

(65) Prior Publication Data
US 2012/0149649 A1      Jun. 14, 2012

(30) Foreign Application Priority Data

Feb. 23, 2010  (JP) .................................. 2010-037014

(51) Int. Cl.
*A61K 47/48* (2006.01)
*C08G 69/10* (2006.01)
*C12N 15/11* (2006.01)

(52) U.S. Cl.
CPC .......... *C08G 69/10* (2013.01); *A61K 47/48323* (2013.01); *A61K 47/48215* (2013.01); *C12N 2310/14* (2013.01); *C12N 15/111* (2013.01); *C12N 2320/32* (2013.01)
USPC ...................................................... 514/21.2

(58) Field of Classification Search
None
See application file for complete search history.

(56) References Cited

U.S. PATENT DOCUMENTS

| | | | |
|---|---|---|---|
| 5,759,827 A | 6/1998 | Legendre et al. | |
| 6,576,254 B1 * | 6/2003 | Uchegbu ....................... | 424/450 |
| 7,780,957 B2 | 8/2010 | Kataoka et al. | |
| 7,829,657 B2 | 11/2010 | Kataoka et al. | |
| 2003/0148929 A1 | 8/2003 | Goto et al. | |
| 2004/0063618 A1 | 4/2004 | Manoharan | |
| 2007/0021590 A1 | 1/2007 | Power et al. | |
| 2007/0059271 A1 | 3/2007 | Kataoka et al. | |
| 2009/0018216 A1 | 1/2009 | Kataoka et al. | |
| 2009/0258416 A1 | 10/2009 | Kataoka et al. | |
| 2009/0291130 A1 | 11/2009 | Ohuchi et al. | |
| 2010/0034886 A1 | 2/2010 | Soula et al. | |
| 2010/0137512 A1 | 6/2010 | Kataoka et al. | |
| 2010/0222407 A1 | 9/2010 | Segura et al. | |
| 2011/0052917 A1 | 3/2011 | Kataoka et al. | |
| 2011/0060123 A1 | 3/2011 | Kataoka et al. | |
| 2012/0053295 A1 | 3/2012 | Kataoka et al. | |

FOREIGN PATENT DOCUMENTS

| | | |
|---|---|---|
| JP | 3-287545 | 12/1991 |
| JP | 9 173067 | 7/1997 |
| JP | 2000 210079 | 8/2000 |
| JP | 2007 527203 | 9/2007 |
| JP | 2008 542500 | 11/2008 |
| JP | 4655298 | 1/2011 |
| WO | 99 61512 | 12/1999 |
| WO | 2005 078084 | 8/2005 |
| WO | 2006 085664 | 8/2006 |
| WO | 2006 115293 | 11/2006 |
| WO | 2007 099660 | 9/2007 |
| WO | 2007 099661 | 9/2007 |
| WO | 2009 113645 | 9/2009 |
| WO | 2009 133968 | 11/2009 |
| WO | 2010 100781 | 9/2010 |

OTHER PUBLICATIONS

Dash et al., Journal of Controlled Release, 1997, 48(2-3), pp. 269-276.*

(Continued)

*Primary Examiner* — Karlheinz R Skowronek
*Assistant Examiner* — Roy Teller
(74) *Attorney, Agent, or Firm* — J-Tek Law PLLC; Jeffrey D. Tekanic

(57) ABSTRACT

The present invention provides a cationic polyamino acid suitable for a carrier that can form a stable complex with a nucleic acid under a physiological condition and release the nucleic acid in cells suitably. The cationic polyamino acid can associate with a nucleic acid and includes a cationic amino acid residue having a cationic group in a side chain and a hydrophobic amino acid residue having a hydrophobic group in a side chain. The cationic polyamino acid includes 1 to 20 units of the cationic amino acid residue and is represented by the following formula (1).

[Chem.1]

$$R^1-(COCHNH)_{m-n}-(COR^{3b}CHNH)_n-(COCHNH)_{x-y}- \\ \phantom{R^1-(COCHNH)_{m-n}-}R^{3a} \phantom{(COR^{3b}CHNH)_n-}\overset{|}{C}=O \phantom{(COCHNH)_{x-y}-}R^{4a} \\ \phantom{R^1-(COCHNH)_{m-n}-}\overset{|}{C}=O \phantom{(COR^{3b}CHNH)_n-}R^{5b} \phantom{(COCHNH)_{x-y}-}\overset{|}{C}=O \\ \phantom{R^1-(COCHNH)_{m-n}-}R^{5a} \phantom{(COR^{3b}CHNH)_n-}R^{6b} \phantom{(COCHNH)_{x-y}-}R^{7a} \\ \phantom{R^1-(COCHNH)_{m-n}-}R^{6a}$$

$$-(COR^{4b}CHNH)_y-(COCHNH)_z-R^2 \\ \phantom{-(COR^{4b}CHNH)_y-}\overset{|}{C}=O \phantom{(COCHNH)_z-}R^8 \\ \phantom{-(COR^{4b}CHNH)_y-}R^{7b}$$

(1)

The meaning of each symbol in the formula is as shown in the description.

23 Claims, 2 Drawing Sheets

(56) References Cited

OTHER PUBLICATIONS

Nakanishi et al., Journal of Controlled Release, 2001, 74, pp. 295-302.*

Kim, H. J. et al., "Introduction of Stearoyl Moieties Into a Biocompatible Cationic Polyaspartamide Derivative, PAsp(DET), With Endosomal Escaping Function for Enhanced siRNA-Mediated Gene Knockdown" Journal of Controlled Release, vol. 145, No. 2, pp. 141-148, (Mar. 30, 2010).

Takemoto, H. et al., Polyion Complex Stability and Gene Silencing Efficiency With A siRNA-Grafted Polymer Delivery System, Biomaterials, vol. 31, No. 31, pp. 8097-8105, (Aug. 7, 2010).

Miyata, K. et al., "Block Catiomer Polyplexes With Regulated Densities of Charge and Disulfide Cross-Linking Directed to Enhance Gene Expression", J. Am. Chem. Soc, vol. 126, pp. 2355-2361, (2004).

Miyata, K. et al., "Polyplexes From Poly(aspartamide) Bearing 1, 2-Diaminoethane Side Chains Induce pH-Selective, Endosomal Membrane Destabilization With Amplified Transfection and Negligible Cytotoxicity", J. Am. Chem. Soc, vol. 130, pp. 16287-16294, (2008).

International Search Report Issued Apr. 12, 2011 in PCT/JP11/053917 filed Feb. 23, 2011.

Extended European Search Report dated Sep. 21, 2012 from related EP application No. 10 741 313.0, including Communication, European Search Opinion, European Search Report and examined claims 1-9.

Takae S et al, "PEG-Detachable Polyplex Micelles Based on Disulfide-Linked Block Catiomers as Bioresponsive Nonviral Gene Vectors", Journal of the Amercican Chemical Society (JACS), vol. 130, Sep. 4, 2008, pp. 6001-6009.

Szokan G & Kotai A, "Basische Derivate von Glutamylpeptiden, III", Acta Chimica Academiae Scientiarum Hungaricae, vol. 88. No. 2. 1976. pp. 137-147.

Makoto Oba et al, "Polyplex Micelles with Cyclic RGD Peptide Ligands and Disulfide Cross-Links Directing to the Enhanced Transfection via Controlled Intracellular Trafficking", Molecular Pharmaceutics, vol. 5, No. 6, Dec. 1, 2008, pp. 1080-1092.

Communication from European Patent office dated Nov. 14, 2012 in counterpart EP application No. 11740552.2, including European search opinion, European Search Report and examined claims 1-5.

* cited by examiner

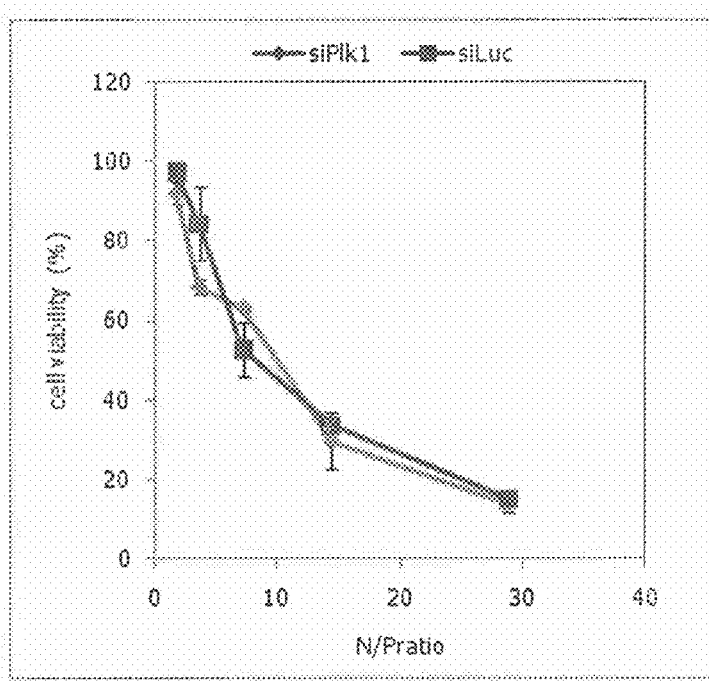

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      sense strand of siRNA for Vargula luciferase including dT
      terminus
<220> FEATURE:
<223> OTHER INFORMATION: Description of Combined DNA/RNA Molecule:
      Synthetic sense strand of siRNA for Vargula luciferase including
      dT terminus

<400> SEQUENCE: 1
cuuacgcuga guacuucgat t                                            21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      antisense strand of siRNA for Vargula luciferase including dT
      terminus
<220> FEATURE:
<223> OTHER INFORMATION: Description of Combined DNA/RNA Molecule:
      Synthetic antisense strand of siRNA for Vargula luciferase
      including dT terminus

<400> SEQUENCE: 2
ucgaaguacu cagcguaagt t                                            21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      antisense strand of Homosapiens siRNA for Plk1 including dT
      terminus
<220> FEATURE:
<223> OTHER INFORMATION: Description of Combined DNA/RNA Molecule:
      Synthetic antisense strand of Homosapiens siRNA for Plk1 including
      dT terminus

<400> SEQUENCE: 3
ccauuaacga gcugcuuaat t                                            21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      antisense strand of Homosapiens siRNA for Plk1 including dT
      terminus
<220> FEATURE:
<223> OTHER INFORMATION: Description of Combined DNA/RNA Molecule:
      Synthetic antisense strand of Homosapiens siRNA for Plk1 including
      dT terminus

<400> SEQUENCE: 4
uuaagcagcu cguuaauggt t                                            21

SHORT-CHAIN CATIONIC POLYAMINO ACID AND USE THEREOF

CROSS-REFERENCE

This application is the US national stage of International Patent Application No. PCT/JP2011/053917 filed on Feb. 23, 2011, which claims priority to Japanese Patent Application No. 2010-037014, filed on Feb. 23, 2010.

TECHNICAL FIELD

The present invention relates to a short-chain cationic polyamino acid, a block copolymer having the polyamino acid, and a polymer particle composition and a complex each obtained using the polyamino acid and/or the block copolymer.

BACKGROUND ART

The application of siRNA to medical treatments is increasingly expected because the siRNA can knock down target mRNA specifically and effectively. However, the development of an effective delivery system is indispensable to apply the siRNA to medical treatments. In recent years, it has been clarified that an therapeutic effect of naked siRNA on age-related macular degeneration (CNV) through its intraocular administration under a clinical trial does not result from a sequence-specific gene knockdown effect induced by siRNA but results from a non-sequence-specific effect via recognition by Toll-like receptor-3 (TLR-3) on cell surface. It has been considered important to develop a carrier that is stable outside cells and is capable of accurately delivering siRNA into the cells in any of in vivo siRNA applications.

Hitherto, a variety of cationic polymers have been provided as carriers for forming a polyion complex (PIC) with DNA and introducing and expressing the nucleic acid in eukaryotic cells. For example, it is known that a poly(L-lysine) derivative in which a hydrophilic group (e.g., polyethylene glycol) and a hydrophobic group (e.g., a palmitoyl group) have been introduced via an ε-amino group of poly(L-lysine) forms a vesicle in the presence of cholesterol in an aqueous medium and the vesicle aggregates gene-containing plasmid DNA to form a stable complex (Patent Document 1). Further, a PIC formed of plasmid DNA with a copolymer derivative whose cation charge and disulfide crosslink density have been adjusted by the thiolation of an ε-amino group of poly(L-lysine) in a poly(L-lysine)-poly(ethylene glycol) copolymer is known to show high stability in an extracellular medium and effectively release the DNA in an intracellular compartment (Non Patent Document 1). Further, it has been confirmed that, when poly(N-[N-(2-aminoethyl)-2-aminoethyl] aspartamide (pAsp (DET))) having an ethylenediamine structure in a side chain and a block copolymer including the pAsp (DET) as one of block components of the block copolymer are produced, such polymers show low cytotoxicity and introduce plasmid DNA into cells with high efficiency to express a gene incorporated into the DNA efficiently (see Non Patent Document 2, Patent Document 2, and Patent Document 3).

As described above, although a carrier effective for a high molecular weight nucleic acid such as DNA has been developed, a carrier capable of forming a stable complex such as a PIC with a low molecular weight nucleic acid such as siRNA as well under a physiological condition and suitably releasing the low molecular weight nucleic acid in cells has not been provided yet.

PRIOR ART DOCUMENTS

Patent Documents

[Patent Document 1] WO 99/61512 A1
[Patent Document 2] WO 2006/085664 A1
[Patent Document 3] WO 2007/099660 A1

Non Patent Documents

[Non Patent Document 1] K. Miyata et al., J. Am. Chem. Soc. 2004, 126, 2355-2361
[Non Patent Document 2] K. Miyata et al., J. Am. Chem. Soc. 2008, 130, 16287-16294

SUMMARY OF INVENTION

Problems to be Solved by the Invention

The present invention has been made in order to solve the conventional problems. A main object of the present invention is to provide a carrier that can form a stable complex with a nucleic acid under a physiological condition and release the nucleic acid in cells suitably.

Means for Solving the Problems

The present invention provides a cationic polyamino acid. The cationic polyamino acid is capable of associating with a nucleic acid and includes a cationic amino acid residue having a cationic group in a side chain and a hydrophobic amino acid residue having a hydrophobic group in a side chain. The cationic polyamino acid includes 1 to 20 units of the cationic amino acid residue and is represented by the following formula (1).

[Chem. 1]

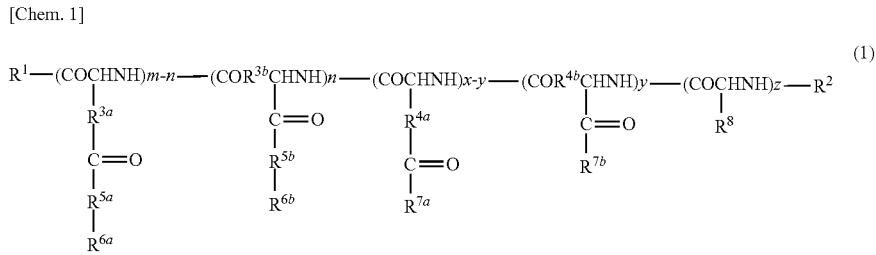

where: $R^1$ represents a hydroxyl group or an unsubstituted or substituted linear or branched alkyloxy group having 1 to 12 carbon atoms, an unsubstituted or substituted linear or branched alkenyloxy group having 2 to 12 carbon atoms, an unsubstituted or substituted linear or branched alkynyloxy group having 2 to 12 carbon atoms, or an unsubstituted or substituted linear or branched alkyl-substituted imino group having 1 to 12 carbon atoms; $R^2$ represents a hydrogen atom, an unsubstituted or substituted linear or branched alkyl group having 1 to 12 carbon atoms, or an unsubstituted or substituted linear or branched alkylcarbonyl group having 1 to 24 carbon atoms; $R^{3a}$, $R^{3b}$, $R^{4a}$, and $R^{4b}$ each independently represent a methylene group or an ethylene group; $R^{5a}$ and $R^{5b}$ each independently represent —O— or —NH—; $R^{6a}$ and $R^{6b}$ each independently represent a saturated or unsaturated linear or branched aliphatic hydrocarbon group having 6 to 27 carbon atoms, an aromatic hydrocarbon group having 6 to 27 carbon atoms, or a steryl group; $R^{7a}$ and $R^{7b}$ are each independently chosen from the same or different groups in the group consisting of the following groups: —NH—$(CH_2)_{p1}$—[NH—$(CH_2)_{q1}$—$]_{r1}NH_2$ (i); —NH—$(CH_2)_{p2}$—N[—$(CH_2)_{q2}$—$NH_2]_2$ (ii); —NH—$(CH_2)_{p3}$—N{[—$(CH_2)_{q3}$—$NH_2$][—$(CH_2)_{q4}$—NH—$]_{r2}H$} (iii); and —NH—$(CH_2)_{p4}$—N{—$(CH_2)_{q5}$—N[—$(CH_2)_{q6}$—$NH_2]_2\}_2$ (iv), where: p1 to p4, q1 to q6, and r1 and r2 each independently represent an integer of 1 to 5; $R^8$ represents a side chain of an amino acid selected from the group consisting of lysine, ornithine, arginine, homoarginine, and histidine; m represents an integer of 5 to 80; n represents an integer of 0 to m; x represents an integer of 1 to 20; y represents an integer of 0 to x; and z represents an integer of 0 to 20, provided that a sum of x and z is 1 or more to 20 or less, the respective repeat units are bound to each other in any suitable order, and $R^{6a}$, $R^{6b}$, $R^{7a}$, $R^{7b}$ and $R^8$ may be optionally selected in each amino acid residue in one polyamino acid.

According to another aspect, the present invention provides a block copolymer. The block copolymer includes the cationic polyamino acid chain segment and the hydrophilic polymer chain segment.

According to yet another aspect, the present invention provides a polymer particle composition. The polymer particle composition includes the cationic polyamino acid and/or the block copolymer.

According to yet another aspect, the present invention provides a complex. The complex includes the cationic polyamino acid and/or the block copolymer, and a nucleic acid.

Advantageous Effects of Invention

According to the present invention, there can be provided the carrier capable of forming a stable complex with a nucleic acid under a physiological condition and suitably releasing the nucleic acid in cells.

BRIEF DESCRIPTION OF DRAWINGS

FIG. 3 is a graph illustrating an activity of a polymer particle composition encapsulating siRNA (Plk1) of a comparative example on MDA-MB-231 cells.

DESCRIPTION OF EMBODIMENTS

A. Cationic Polyamino Acid

Figure 1:
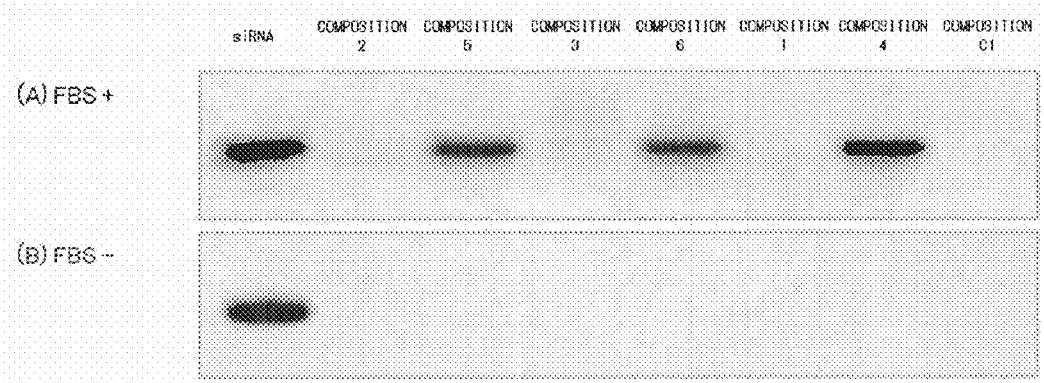
FIG. 1 show gel images after electrophoresis of polymer particle compositions each encapsulating siRNA (Luc).

A cationic polyamino acid of the present invention includes a cationic amino acid residue having a cationic group in a side chain and a hydrophobic amino acid residue having a hydrophobic group in a side chain, and is capable of associating with a nucleic acid. The "capable of associating with a nucleic acid" as used herein means being capable of interacting with a nucleic acid to form a complex (for example, a polyion complex (PIC)) under a physiological condition at pH 7.4. Further, the nucleic acid means a poly- or oligonucleotide including nucleotides formed of a purine or pyrimidine base, a pentose, and phosphoric acid as basic units. Further, an amino acid from which the amino acid residue is derived may be any suitable compound as long as the amino acid has both functional groups of an amino group and a carboxyl group, and the amino acid may form a polyamino acid via an amide bond (peptide bond).

The number of cationic amino acid residues included in the cationic polyamino acid of the present invention is 1 to 20, preferably 1 to 15, more preferably 1 to 10, particularly preferably 1 to 5. The number of hydrophobic amino acid residues included in the cationic polyamino acid is preferably 1 to 80, more preferably 5 to 70, particularly preferably 10 to 60. According to the cationic polyamino acid of the present invention, the cationic polyamino acid has a cationic amino acid residue and hence can be electrostatically bound to a nucleic acid as an anionic molecule, and further the number of amino acid residues is set to 20 or less, and hence the bond can be prevented from being excessively strengthened. As a result, the nucleic acid can be appropriately released. In other words, in one embodiment, the present invention relates to a cationic polyamino acid base material capable of associating with a nucleic acid, the cationic polyamino acid base material including: a cationic amino acid residue having a cationic group in a side chain; and a hydrophobic amino acid residue having a hydrophobic group in a side chain, in which the number of the cationic amino acid residues is restricted in the range of 1 to 20 to promote the desorption (release) of a nucleic acid from the base material. When the number of the cationic amino acid residues included in the cationic polyamino acid is restricted in the range of 15 or less, further 10 or less and a given kind of cationic amino acid residue is selected, the nucleic acid tends to be released appropriately. The given kind of cationic amino acid residue may be exemplified by a cationic group excluding L-lysine, more specifically, a group derived from diethylenetriamine which is represented by each of $R^{7a}$ and $R^{7b}$ in the chemical formula (1) described later. In other words, the cationic polyamino acid base material according to the present invention is a cationic polyamino acid base material capable of associating with a nucleic acid, the cationic polyamino acid base material including: a cationic amino acid residue having a cationic group in a side chain; and a hydrophobic amino acid residue having a hydrophobic group in a side chain, in which the cationic amino acid residue is formed of a cationic group excluding L-lysine (e.g., a group derived from diethylenetriamine which is represented by each of $R^{7a}$ and $R^{7b}$ in the chemical formula (1) described later) and the number of the cationic amino acid residues may be restricted in the range of 1 to 15, further 1 to 10. When the number of the cationic amino acid residues included in the cationic polyamino acid is 2 or more, the stability of the complex may be improved. Further, according to the cationic polyamino acid of the present invention, the cationic polyamino acid has a hydrophobic amino acid residue and hence gives a hydrophobic interaction, and as a result, the stability of a complex with a nucleic acid is improved, which allows the formation of a stable complex with a small molecular weight nucleic acid as well. In addition, the hydrophobic amino acid residue sticks into a hydrophobic moiety on a cell membrane and can function as an anchor for fixing a base material on a cell membrane, leading to an improvement in nucleic acid introduction rate into cells.

An amino acid from which the cationic amino acid residue is derived is, for example, an amino acid having a pKa value, which is defined owing to an amino group in a side chain structure excluding a main skeleton of an amino acid, of, for example, 3 to 13, preferably 4 to 12, more preferably 5 to 11.

An amino acid from which the hydrophobic amino acid residue is derived is preferably exemplified by an amino acid having solubility in 100 g of water at 25° C. of 5 g or less, more preferably 4 g or less. Examples of such amino acid include a non-polar natural amino acid such as leucine, isoleucine, phenylalanine, methionine, or tryptophan and a hydrophobic derivative of an amino acid in which a hydrophobic group has been introduced in a side chain. A preferred example of the hydrophobic derivative of an amino acid is a hydrophobic derivative of an acidic amino acid such as aspartic acid or glutamic acid. In other words, the cationic polyamino acid base material according to the present invention is a cationic polyamino acid base material capable of associating with a nucleic acid, the cationic polyamino acid base material including: a cationic amino acid residue having a cationic group in a side chain; and a hydrophobic amino acid residue having a hydrophobic group in a side chain, in which the hydrophobic amino acid residue is formed of a group derived from i) a non-polar natural amino acid chosen from leucine, isoleucine, phenylalanine, methionine, and tryptophan or ii) a hydrophobic derivative of an acidic amino acid chosen from aspartic acid and glutamic acid, the cationic amino acid residue is formed of a cationic group excluding L-lysine (e.g., a group derived from diethylenetriamine which is represented by each of $R^{7a}$ and $R^{7b}$ in the chemical formula (1) described later), and the number of the cationic amino acid residues may be restricted in the range of 1 to 15, further 1 to 10.

The hydrophobic group to be introduced may be preferably exemplified by a saturated or unsaturated linear or branched aliphatic hydrocarbon group having 6 to 27 carbon atoms, an aromatic hydrocarbon group having 6 to 27 carbon atoms, or a steryl group.

The cationic polyamino acid of the present invention may include, as necessary, any other amino acid residue (e.g., an acidic amino acid residue such as an aspartic acid residue or a glutamic acid residue) excluding the cationic amino acid residue and hydrophobic amino acid residue.

The number of moles of the amino groups included in 1 g of the cationic polyamino acid of the present invention may be, for example, 0.1 mmol to 10 mmol, for example, 0.2 mmol to 5 mmol, or, for example, 0.4 mmol to 3 mmol.

The cationic polyamino acid of the present invention may be preferably represented by the following formula (1):

in the formula: $R^1$ represents a hydroxyl group, an unsubstituted or substituted linear or branched alkyloxy group having 1 to 12 carbon atoms, an unsubstituted or substituted linear or branched alkenyloxy group having 2 to 12 carbon atoms, an unsubstituted or substituted linear or branched alkynyloxy group having 2 to 12 carbon atoms, or an unsubstituted or substituted linear or branched alkyl-substituted imino group having 1 to 12 carbon atoms;

$R^2$ represents a hydrogen atom, an unsubstituted or substituted linear or branched alkyl group having 1 to 12 carbon atoms, or an unsubstituted or substituted linear or branched alkylcarbonyl group having 1 to 24 carbon atoms;

$R^{3a}$, $R^{3b}$, $R^{4a}$, and $R^{4b}$ each independently represent a methylene group or an ethylene group;

$R^{5a}$ and $R^{5b}$ each independently represent —O— or —NH—;

$R^{6a}$ and $R^{6b}$ each independently represent a saturated or unsaturated linear or branched aliphatic hydrocarbon group having 6 to 27 carbon atoms, an aromatic hydrocarbon group having 6 to 27 carbon atoms, or a steryl group;

$R^{7a}$ and $R^{7b}$ are each independently chosen from the same or different groups in the group consisting of the following groups:

—NH—$(CH_2)_{p1}$—[NH—$(CH_2)_{q1}$—]$_{r1}$NH$_2$ (i);
—NH—$(CH_2)_{p2}$—N[—$(CH_2)_{q2}$—NH$_2$]$_2$ (ii);
—NH—$(CH_2)_{p3}$—N{[—$(CH_2)_{q3}$—NH$_2$][—$(CH_2)_{q4}$—NH—]$_{r2}$H} (iii); and
—NH—$(CH_2)_{p4}$—N{—$(CH_2)_{q5}$—N[—$(CH_2)_{q6}$—NH$_2$]$_2$}$_2$ (iv), where p1 to p4, q1 to q6, and r1 and r2 each independently represent an integer of 1 to 5;

$R^8$ represents a side chain of an amino acid selected from the group consisting of lysine, ornithine, arginine, homoarginine, and histidine;

m represents an integer of 5 to 80;
n represents an integer of 0 to m;
x represents an integer of 1 to 20;
y represents an integer of 0 to x;
z represents an integer of 0 to 20, provided that the sum of x and z is 1 or more to 20 or less, the respective repeat units are bound to each other in any suitable order, and $R^{6a}$, $R^{6b}$, $R^{7a}$, $R^{7b}$, and $R^8$ may be optionally selected in each amino acid residue in one polyamino acid.

In the formula (1), an alkyl moiety in the linear or branched alkyloxy group having 1 to 12 carbon atoms, alkyl-substituted imino group having 1 to 12 carbon atoms, and alkyl group having 1 to 12 carbon atoms, which are defined by the groups $R^1$ and $R^2$, may be, for example, a methyl group, an ethyl group, an n-propyl group, an isopropyl group, an n-butyl group, an sec-butyl group, a tert-butyl group, an n-hexyl group, a decyl group, and an undecyl group. An alkenyl or alkynyl moiety in the linear or branched alkenyloxy group having 2 to 12 carbon atoms or the linear or branched alky-

[Chem. 2]

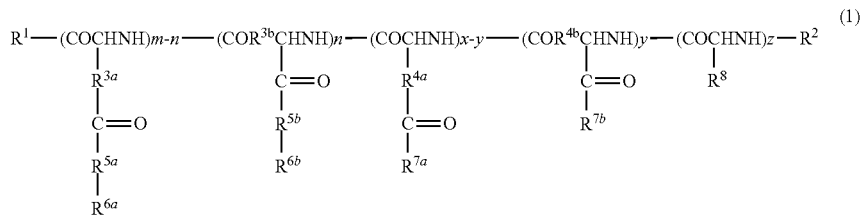

(1)

nyloxy group having 2 to 12 carbon atoms may be exemplified by one including a double bond or a triple bond in the alkyl group having 2 or more carbon atoms as exemplified above.

For such group or moiety, a substituent in a "substituted" case may be exemplified by, but not limited to, a $C_{1-6}$ alkoxy group, an aryloxy group, an aryl $C_{1-3}$ oxy group, a cyano group, a carboxyl group, an amino group, a $C_{1-6}$ alkoxycarbonyl group, a $C_{2-7}$ acylamide group, a tri-$C_{1-6}$ alkyl siloxy group, a siloxy group, or a silylamino group, or may be exemplified by an acetalized formyl group, a formyl group, or a halogen atom such as chlorine or fluorine. In this context, for example, the expression "$C_{1-6}$" means 1 to 6 carbon atoms and is used with the same meaning in the following description. In addition, an unsubstituted or substituted linear or branched alkyl moiety having 1 to 12 carbon atoms in the unsubstituted or substituted linear or branched alkylcarbonyl group having 1 to 24 carbon atoms may be selected with reference to the examples, and an alkyl moiety having 13 or more carbon atoms may be, for example, a tridecyl group, a tetradecyl group, a pentadecyl group, a nonadecyl group, a docosanyl group, and a tetracosyl group.

Repeat units having the groups $R^{3a}$, $R^{3b}$, $R^{4a}$, and $R^{4b}$ are bound to each other in any suitable order, and a random structure or a block structure may be applicable. When both of $R^{3a}$ and $R^{3b}$ represent an ethylene group, a polyamino acid in which n represents an integer of 0 or a polyamino acid in which m-n represents an integer of 0 is typically represented. The former represents, for example, poly-α-glutamic acid, which is obtained by the polymerization of an N-carboxylic anhydride of glutamic acid γ-benzyl ester, and the latter represents, for example, poly-γ-glutamic acid, which is produced by a bacterial strain of the genus *Bacillus* bacteria such as *Bacillus natto*. Meanwhile, when both of $R^{3a}$ and $R^{3b}$ each represent a methylene group, it is understood that the respective repeat units having those groups may coexist with each other. The same holds true for $R^{4a}$ and $R^{4b}$. It is preferred that $R^{3a}$ and $R^{3b}$ each represent an ethylene group and $R^{4a}$ and $R^{4b}$ each represent a methylene group from the viewpoint of production efficiency.

When the aliphatic hydrocarbon group, which is defined for each of the groups $R^{6a}$ and $R^{6b}$, is saturated, the group is equivalent to an alkyl group having 6 to 27 carbon atoms and is exemplified by a pentacosyl group, a hexacosyl group, or a heptacosyl group as well as the alkyl group. The unsaturated aliphatic hydrocarbon group corresponds to a group in which 1 to 5 carbon-carbon single bonds in a chain of the alkyl group are replaced by carbon-carbon double bonds. An unsaturated aliphatic hydrocarbon from which such group is derived may be exemplified by, but not limited to, lauric acid (or dodecanoic acid), myristic acid (or tetradecanoic acid), palmitic acid (or hexadecanoic acid), palmitoleic acid (or 9-hexadecenoic acid), stearic acid (or octadecanoic acid), oleic acid, linoleic acid, linolenic acid, eleostearic acid (or 9,11,13-octadecatrienoic acid), arachidic acid, arachidonic acid, behenic acid, lignoceric acid, nervonic acid, cerotic acid, or montanic acid.

Examples of the aromatic hydrocarbon group having 6 to 27 carbon atoms, which is defined for each of the groups $R^{6a}$ and $R^{6b}$, include such as an aryl group and an aralkyl group. Preferred specific examples thereof include such as a phenyl group, a naphthyl group, a tolyl group, a xylyl group, a benzyl group, and a phenethyl group.

A sterol from which a steryl group, which is defined for each of the groups $R^{6a}$ and $R^{6b}$, is derived, means a natural compound, a semisynthetic compound, or a synthetic compound based on a cyclopentanone hydrophenanthrene ring ($C_{17}H_{28}$) and derivatives thereof. For example, a natural sterol is exemplified by, but not limited to, cholesterol, cholestanol, dihydrocholesterol, cholic acid, campesterol, or sitosterol. Semisynthetic or synthetic compounds thereof may be, for example, synthetic precursors of above natural products (as necessary, encompassing a compound in which part or all of, if present, certain functional groups, hydroxy groups have been protected with a hydroxy protective group known in the art, or a compound in which a carboxyl group has been protected with carboxyl protection). Further, the sterol derivative means that, for example, without adversely affecting the object of the present invention, a $C_{1-12}$ alkyl group, a halogen atom such as chlorine, bromine, or fluorine may be introduced into a cyclopentanone hydrophenanthrene ring, and the ring system may be saturated or partially unsaturated. A sterol from which the steryl group is derived is preferably a sterol of an animal or vegetable oil origin such as cholesterol, cholestanol, dihydrocholesterol, cholic acid, campesterol, or sitosterol, more preferably cholesterol, cholestanol, or dihydroxycholesterol, particularly preferably cholesterol.

The group chosen from the group consisting of:
—NH—$(CH_2)_{p1}$—[NH—$(CH_2)_{q1}$—$]_{r1}$NH$_2$ (i);
—NH—$(CH_2)_{p2}$—N[—$(CH_2)_{q2}$—NH$_2$]$_2$ (ii);
—NH—$(CH_2)_{p3}$—N{[—$(CH_2)_{q3}$—NH$_2$][—$(CH_2)_{q4}$—NH—]$_{r2}$H} (iii); and
—NH—$(CH_2)_{p4}$—N{—$(CH_2)_{q5}$—N[—$(CH_2)_{q6}$—NH$_2$]$_2$}$_2$ (iv),
which is defined for each of the groups $R^{7a}$ and $R^{7b}$, is preferably the same group, more preferably the group of the formula (1). Further, p1 to p4 and q1 to q6 each independently represent preferably 2 or 3, more preferably 2. Meanwhile, it is preferred that r1 and r2 each independently represent an integer of 1 to 3.

m-n and n each represent the number of repeat of hydrophobic amino acid residues, x-y, y, and z each represent the number of repeat of cationic amino acid residues. x represents preferably 1 to 20, preferably 1 to 15, more preferably 1 to 10, particularly preferably 1 to 5. When x represents 1 or more, the polyamino acid of the present invention has at least the group $R^{7a}$ or $R^{7b}$. The group $R^{7a}$ or $R^{7b}$ has a plurality of different amine functional groups and hence shows a plurality of stages of pKa, and a plurality of amine functional groups are partially protonated under a physiological condition at pH 7.4 and may interact with a nucleic acid to suitably form a complex (for example, a PIC). Further, the complex thus formed is integrated into an endosome (pH 5.5) to reduce the pH, the protonation of the cationic polyamino acid further proceeds, and endosomal escape may be promoted based on a buffer effect (or a proton sponge effect). As a result, it is possible to reduce damages on cells.

The respective repeat units in the formula (1) are bound to each other in any suitable order, and a random structure or a block structure may be applicable. The cationic polyamino acid is of block type including the segment formed of a cationic amino acid residue and segment formed of a hydrophobic amino acid residue. Hence, when the cationic polyamino acid of block type is used as a base material to form a complex with a nucleic acid, the introduction of the nucleic acid into cells is promoted and an ability to retain a nucleic acid in a base material may be ensured while the release of the nucleic acid from the base material is promoted.

The cationic polyamino acid represented by the formula (1) may be produced, for example, by producing a polyamino acid ester through the polymerization of an N-carboxylic anhydride (NCA) of a protected amino acid such as β-benzyl-L-aspartate, γ-benzyl-L-glutamate, or Nε-Z-L-lysine known per se, and then carrying out aminolysis using a polyamine corresponding to the groups $R^{7a}$, $R^{7b}$, and $R^8$ to introduce a cationic group into a side chain of a polyamino acid.

In one embodiment, when a polymer obtained by the polymerization of γ-benzyl-L-glutamate and the subsequent polymerization of β-benzyl-L-aspartate is subjected to a reaction with an amine compound such as diethylenetriamine (DET), an ester-amide exchange reaction occurs preferentially for poly (β-benzyl-L-aspartate) and an amine residue such as a DET group is introduced into an aspartic acid side chain. As a result, a block type cationic polyamino acid formed of an aspartic acid-derived cationic amino acid residue segment having a cationic group introduced into a side chain and a glutamic acid-derived hydrophobic amino acid residue segment having a benzyl group introduced into a side chain may be obtained. Meanwhile, β-benzyl-L-aspartate and γ-benzyl-L-glutamate are simultaneously polymerized and then subjected to a reaction with an amine compound such as diethylenetriamine (DET), a random type cationic polyamino acid in which an aspartic acid-derived cationic amino acid residue having a cationic group introduced into a side chain and a glutamic acid-derived hydrophobic amino acid residue having a benzyl group introduced into a side chain are optionally arranged may be obtained.

A part of amino acid ester residues may undergo a structural change by nucleophilic attack of an amine (for example, imide ring formation through the dealcoholization of an amino acid ester residue) during the synthesis process. In this description, a cationic polyamino acid further including residues that have undergone such structural change is also included in the general formula (1). In this case, the number of the residues that have undergone a structural change is excluded from the number of cationic amino acid residues and the number of hydrophobic amino acid residues. Further, part of NH groups and $NH_2$ groups in the cationic amino acid residues may be converted into a salt (mainly a hydrochloride) by use of an acid (mainly hydrochloric acid) during the synthesis process. In this description, a cationic polyamino acid including such structure is also included in the general formula (1). In other words, part of NH groups and $NH_2$ groups in the groups $R^{7a}$, $R^{7b}$, and $R^8$ may be in a form of a salt (for example, a hydrochloride).

B. Block Copolymer

The block copolymer of the present invention includes a segment formed of the cationic polyamino acid described in the section A and a hydrophilic polymer chain segment. Such configuration allows the block copolymer of the present invention to form polymer particles (for example, polymer micelles) each having enhanced retention capacity in circulating blood while retaining at least the characteristics possessed by the cationic polyamino acid itself.

Any appropriate hydrophilic polymer may be employed as the hydrophilic polymer. Examples of the hydrophilic polymer include poly(ethylene glycol), polysaccharide, poly(vinylpyrrolidone), poly(vinyl alcohol), poly(acrylic amide), poly(acrylic acid), poly(methacrylic amide), poly(methacrylic acid), poly(methacrylic acid ester), poly(acrylic acid ester), polyamino acid, poly(malic acid), and derivatives thereof. Specific examples of the polysaccharide include starch, dextran, fructan, and galactan. Of those, for poly(ethylene glycol), end-reactive polyethylene glycols having a variety of functional groups at their ends are sold on the market. Further, polyethylene glycols having a variety of molecular weights are sold on the market and are easily available, and hence may be preferably used.

The block copolymer of the present invention may be preferably represented by the following formula (2) or (3):

[Chem. 3]

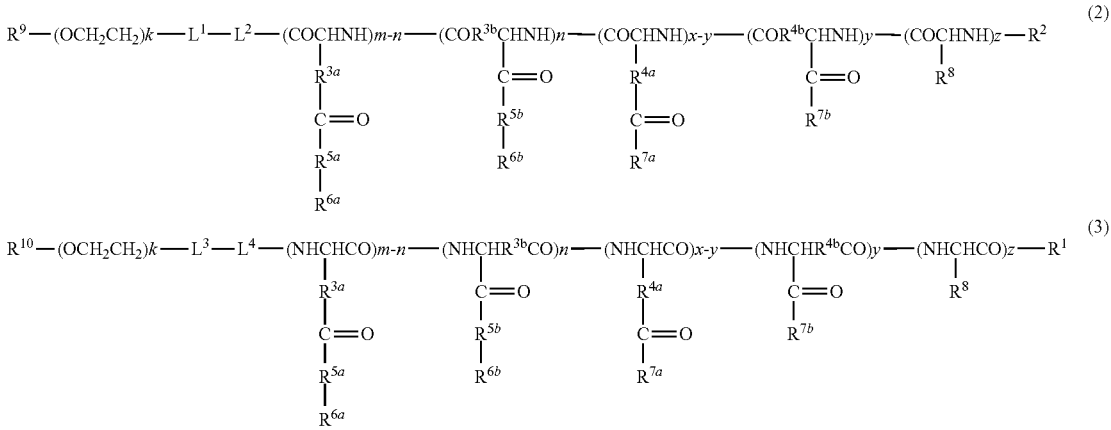

glutamic acid-derived hydrophobic amino acid residue having a benzyl group introduced into a side chain are optionally arranged may be obtained.

in each of the formulae: $R^1$ to $R^8$, m-n, n, x-y, y, and z have the same meanings as those defined for the formula (1);

$L^1$ and $L^3$ each independently represent —S—S— or a valence bond;

$L^2$ represents —NH—, —O—, —O(CH$_2$)$_{p1}$—NH—, or —$L^{2a}$—(CH$_2$)$_{q1}$—$L^{2b}$—, where p1 and q1 each independently represent an integer of 1 to 5, $L^{2a}$ represents OCO, OCONH, NHCO, NHCOO, NHCONH, CONH, or COO, and $L^{2b}$ represents NH or O;

$L^4$ represents —OCO—(CH$_2$)$_{p2}$—CO—, —NHCO—(CH$_2$)$_{p3}$—CO—, or —$L^{4a}$—(CH$_2$)$_{q2}$—CO—, where p2, p3, and q2 each independently represent an integer of 1 to 5 and $L^{4a}$ represents OCONH, —CH$_2$NHCO—, NHCOO, NHCONH, CONH, or COO;

$R^9$ and $R^{10}$ each independently represent a hydrogen atom or an unsubstituted or substituted linear or branched alkyl group having 1 to 12 carbon atoms; and k represents an integer of 30 to 20,000.

$L^1$ and $L^3$ above each independently represent —S—S— or a valence bond. Meanwhile, $L^2$ represents —NH—, —O—, —O(CH$_2$)$_{p1}$—NH—, or —$L^{2a}$—(CH$_2$)$_{q1}$—$L^{2b}$—, where p1 and q1 each independently represent an integer of 1 to 5, $L^{2a}$ represents OCO, OCONH, NHCO, NHCOO, NHCONH, CONH, or COO and $L^{2b}$ represents NH or O. Further, $L^4$ represents —OCO—$(CH_2)_{p2}$—CO—, —NHCO—$(CH_2)_{p3}$—CO—, or —$L^{4a}$—$(CH_2)_{q2}$—CO— where p2, p3, and q2 each independently represent an integer of 1 to 5, $L^{4a}$ represents OCONH, —$CH_2$NHCO—, NHCOO, NHCONH, CONH, or COO. In the definition, both of $L^1$ and $L^2$ and both of $L^3$ and $L^4$ each need to be combined together so as to form one linking group. For example, when $L^2$ represents —NH—, $L^1$ does not represent —S—S— but a valence bond. A preferable example of the combination includes a combination capable of forming a linking group when $L^1$ or $L^3$ represents —S—S—.

Examples of the linear or branched alkyl group having 1 to 12 carbon atoms, which is defined by each of the groups $R^9$ and $R^{10}$, include the same group as the alkyl moiety of the linear or branched alkyloxy group having 1 to 12 carbon atoms, alkyl-substituted imino group having 1 to 12 carbon atoms, and alkyl group having 1 to 12 carbon atoms, which is defined by each of the groups $R^1$ and $R^2$ in the formula (1). Further, the same holds true for the substituent.

k, which represents the number of repeat of ethylene glycol (or oxyethylene), represents an integer of 30 to 20,000, preferably 40 to 2,000, more preferably 50 to 1,000.

The block copolymer of the present invention may be formed, for example, by coupling together the cationic polyamino acid and hydrophilic polymer by a known method without any further treatment or as necessary after purification for narrowing molecular weight distribution. Further, for example, the block copolymer of the general formula (2) may be produced by forming a polyethylene glycol chain by anion living polymerization using an initiator capable of providing $R^9$, then introducing an amino group at the growing end side, polymerizing from the amino end an N-carboxylic anhydride (NCA) of a protected amino acid such as β-benzyl-L-aspartate, γ-benzyl-L-glutamate, or Nε-Z-L-lysine, and introducing a cationic group into a side chain of the resultant polyamino acid. As mentioned above, a structure change (for example, imide ring formation due to the dealcoholization of amino acid ester residues) may occur by the nucleophilic attack of a polyamine in part of amino acid ester residues during the synthesis process of a cationic polyamino acid. In this description, a block copolymer including residues that have undergone such structural change is also included in the general formulae (2) and (3). Further, part of NH groups and $NH_2$ groups in the cationic amino acid residue may be formed into a salt (mainly a hydrochloride) by use of an acid (mainly hydrochloric acid) during the synthesis process. In this description, a block copolymer including such structure is also included in the general formulae (2) and (3).

C. Polymer Particle Composition

The polymer particle composition of the present invention includes the cationic polyamino acid described in the section A and/or the block copolymer described in the section B. The cationic polyamino acid (block type/random type) and block copolymer may associate in an aqueous solution to suitably form polymer particles when the ratio of a hydrophobic amino acid residue in a cationic polyamino acid becomes high. In the present invention, an assembly in which a plurality of molecules assemble to form particulates is also encompassed in particles and such polymer assembly is also referred to as polymer particles. The polymer particles each have an average particle diameter of, for example, 5 nm to 5 μm, preferably 5 to 500 nm, more preferably 10 to 300 nm.

The polymer particle composition of the present invention may include any other polymer excluding the cationic polyamino acid and block copolymer as long as the effect of the present invention can be obtained. Examples of the any other polymer include a block copolymer having a hydrophilic polymer chain segment and a hydrophobic polymer chain segment. Such block copolymer can suitably associate in an aqueous solution to form stable polymer particles (for example, polymer micelles) and the coexistence thereof can afford a polymer particle composition excellent in stability. Such effect may be particularly suitably exerted in a polymer particle composition including a cationic polyamino acid free of a hydrophilic polymer chain segment. The other block copolymer is, for example, the polymer described in WO 2004/082718 A1.

The weight ratio of the cationic polyamino acid and block copolymer to the other polymer in the polymer particle composition of the present invention may be properly set depending on the polymer's character. The weight ratio may be, for example, 20:1 to 1:20, preferably 10:1 to 1:10, more preferably 1:5 to 5:1.

A method of preparing the polymer particle composition of the present invention is not particularly limited and the polymer particle composition may be prepared, for example, by adding an aqueous medium such as water or a buffer to a polymer of interest, stirring the mixture, applying ultrasound, pressure, shear force, or physical energy which is a combination thereof, or dissolving the polymer of interest in a volatile organic solvent, then evaporating the organic solvent to dryness, adding the aqueous medium thereto, and applying such physical energy as described above. Alternatively, the polymer particle composition may also be prepared by adding to a polymer of interest a water-soluble organic solvent capable of dissolving the polymer to dissolve the polymer, and carrying out dialysis against the aqueous medium. In the context, examples of the volatile organic solvent may include methanol, ethanol, acetone, chloroform, acetonitrile, tetrahydrofuran, and dichloromethane. Further, examples of the water-soluble organic solvent include methanol, ethanol, acetonitrile, dimethylsulfoxide, N,N-dimethylformamide, and N,N-dimethylacetamide.

D. Complex

The complex of the present invention includes the cationic polyamino acid described in the section A and/or the block copolymer described in the section B, and a nucleic acid. The cationic polyamino acid and block copolymer each have a cationic group and hence may form a complex (for example, a PIC) with an anion charged compound under a physiological condition. Examples of the anion charged compound include a protein, a lipid, a peptide, and a nucleic acid. Of those, the cationic polyamino acid and block copolymer may form a complex with a nucleic acid suitably. As described in Examples later, a complex formed of the cationic polyamino acid or block copolymer and nucleic acid releases the nucleic acid during the FBS treatment in different ways depending on whether the structure of the cationic polyamino acid is of block type or of random type, and hence a polymer having an appropriate structure may be selected depending on purposes.

As described above, the cationic polyamino acid has a hydrophobic group in a side chain, and hence the cationic polyamino acid and a block copolymer having the polyamino acid can form a complex with a small molecular weight nucleic acid as well under a physiological condition to provide a stable vesicle or associate. The nucleic acid capable of forming a complex with the cationic polyamino acid or block copolymer means a poly- or oligonucleotide including as a basic units nucleotides formed of a purine or pyrimidine base, a pentose, and phosphoric acid, and examples thereof may include oligo- or poly-double-stranded RNA, oligo- or poly-double-stranded DNA, oligo- or poly-single-stranded DNA, and oligo- or poly-single-stranded RNA. Further, oligo- or poly-double-stranded nucleic acid and oligo- or poly-single-stranded nucleic acid in each of which RNA and DNA exist in a mixed state in the same chain are also included. Further, the nucleotide contained in the nucleic acid may be of natural type or of chemically modified non-natural type, or may have added thereto an amino group, a thiol group, a fluorescent compound or any other molecule. The nucleic acid is not limited but may be formed of 4 to 20,000 bases, preferably 10 to 10,000 bases, more preferably 18 to 30 bases. Further, in consideration of functions or actions, there may be given plasmid DNA, siRNA, micro RNA, shRNA, an antisense nucleic acid, a decoy nucleic acid, an aptamer, and a ribozyme.

As the siRNA, for example, all of those designed for a target gene or a target polynucleotide by a known method may be used. For the chain length of siRNA, a moiety for forming a double strand may have a length of preferably 15 to 50 bases, more preferably 18 to 30 bases, and compounds known in the art and all nucleotides having the same actions or functions as those compounds are encompassed. Specific examples of the siRNA may be designed with reference to a gene which may serve as a target of a gene therapy, but are not limited thereto. Examples of such gene may include, but not limited to, PKCα related to a disease such as non-small cell lung carcinoma, BCL-2 related to a disease such as malignant melanoma, ICAM-1 related to Crohn's disease, HCV related to hepatitis C, TNFα related to rheumatoid arthritis or psoriasis, adenosine AI receptor related to asthma, c-raf kinase related to a disease such as ovary cancer, H-ras related to a disease such as pancreas cancer, c-myc related to coronary artery disease, PKA Ria related to large bowel cancer, HIV related to AIDS, DNA methyl transferase related to solid cancer, VEGF receptor related to cancer, ribonucleotide reduction enzyme related to kidney cancer, CMV IE 2 related to CMV retinitis, MMP-9 related to prostate cancer, TGFβ2 related to malignant glioma, CD 49 d related to Multiple Sclerosis, PTP-1B related to diabetes, c-myb related to cancer, EGFR related to a disease such as breast cancer, mdr1 related to cancer, autotaxin and GLUT-1 gene. In the same manner as for the antisense nucleic acid, those known in the art or all having the same functions or actions as those may be employed as a target for forming a complex in accordance with the present invention.

The complex of the present invention when the nucleic acid is siRNA preferably has an N/P ratio of 2 or more from the viewpoint of improving stability under a physiological condition, and the N/P ratio is preferably 200 or less from the viewpoint of inhibiting toxicity due to a polymer. The meaning of the N/P ratio is described later.

When the cationic polyamino acid is used to provide a complex with siRNA, an optimum N/P ratio cannot be specified because it varies depending on the ratio of hydrophobic groups in the total amino groups, but the N/P ratio is generally 5 or more, preferably 7 or more. When a complex with siRNA is formed at such N/P ratio, there can be provided stable associates each having an average particle diameter ranging from about 5 nm to about 300 nm under a physiological condition such as circulating blood. Such complex may be prepared by mixing the cationic polyamino acid and siRNA so as to achieve the N/P ratio, as necessary, in a buffered aqueous solution. Further, such complex may be prepared, for example, by mixing siRNA with a polymer particle composition including the cationic polyamino acid described in the section C so as to achieve a desired N/P ratio and leaving the mixture to stand still so that siRNA is encapsulated in polymer particles.

When a complex with siRNA is obtained using the block copolymer and the ratio of a hydrophobic amino acid residue in the cationic polyamino acid segment of the block copolymer becomes high, a stable complex may be formed at a broader N/P ratio as compared to the case of using the cationic polyamino acid itself. This is because such copolymer tends to form polymer particles (for example, polymer micelles) in an aqueous solution by self-association. Such complex may be prepared, for example, by mixing siRNA with a polymer particle composition including the block copolymer described in the section C so as to achieve a desired N/P ratio and leaving the mixture to stand still to encapsulate siRNA into polymer particles.

The complex may be used as it is, or may be used by being encapsulated in any appropriate carrier which may be used as a carrier for a drug delivery system (DDS). Typical examples of such carrier include polymer micelles and liposomes. The encapsulation into a DDS carrier prevents, for example, blood components from clumping around a complex, which allows the appropriate release of a nucleic acid suitably. Such effect may be exerted particularly suitably in a complex including the cationic polyamino acid and nucleic acid.

EXAMPLES

In the following examples, polymer structures are described in the order of the molecular weight (kMw) of PEG, the polymerization degree of PBLG, and the polymerization degree of PBLA or its derivative. For example, when PEG had a molecular weight of 10,000, PBLG had a polymerization degree of 35, and PBLA had a polymerization degree of 5, the polymer is abbreviated as "PEG-PBLG-PBLA 10-35-5". In this context, the polymerization degree of each amino acid residue is a statistical value and may have a range of values. Thus, the value abbreviated as described above may have a variation of a few units (for example, about ±2 units) from an actually measured value. Further, a polymer having a regular amino acid residue sequence in a polyamino acid, which is obtained by the polymerization of PBLG and the subsequent polymerization of PBLA, is abbreviated as Block polymer based on its structure. Further, a polymer having a random amino acid residue sequence in a polyamino acid, which is obtained by the simultaneous addition and polymerization of PBLG and PBLA, is abbreviated as Random polymer based on its polymer structure. Unless indicated otherwise, methods of analyzing the respective characteristics in Examples are as described below.

(1) Nuclear Magnetic Resonance Spectrum ($^1$H-NMR)

Measurement was performed using a nuclear magnetic resonance apparatus (manufactured by JEOL Ltd., JEOL AL300 (300 MHz)) under conditions of solvent: DMSO-$d_6$ and measurement temperature: 25° C.

(2) Amino Acid Analysis

As described below, concentrations of poly(β-benzyl-L-glutamate) (PBLG) and poly(N-[N-(2-aminoethyl)-2-aminoethyl]aspartamide (pAsp (DET)) in a polymer were determined by subjecting the polymer to acid hydrolysis and measuring as a glutamic acid (Glu) and as an aspartic acid (Asp) in accordance with the Waters AccQ•Tag™ amino acid analysis method manual (Nihon Waters K.K.).

(2-1) Acid Hydrolysis 10 mg of a polymer were fractionated in a glass test tube equipped with a screw cap, and 6 N hydrochloric acid was added so as to achieve a polymer concentration of 5 mg/mL. The acid hydrolysis of the polymer was performed by subjecting the solution to heat treatment at 105° C. for 19 hours. Then, to a 1.5 mL microtube were added 300 μL of 4 N NaOH, 500 μL of ultrapure water, and 200 μL of the resultant acid hydrolyzed solution for neutralization, and the mixture was filtered with a 0.22-μm filter (Nihon Millipore K.K., registered trademark "Millex" GV 13 mm Φ). The filtrate was then diluted 50-fold with ultrapure water to prepare a sample solution.

(2-2) Amino Acid Analysis

To a 1.5 mL microtube were added 70 μL of an AccQ•Fluor Borate Buffer and 10 μL of the sample solution obtained in the section (2-1), and the mixture was stirred with a vortex mixer. 20 μL of an AccQ•Fluor Reagent were then added and the mixture was stirred with a vortex mixer for 15 seconds immediately after the addition to prepare an HPLC measurement sample. HPLC conditions are as described below. Further, unless indicated otherwise, all HPLC analyses were carried out under the same conditions.

[HPLC Conditions]
System: Waters HPLC system (Waters Alliance System, 2695, 2475, 2996)
Column: AccQ•Tag™ Column for hydrolysate amino acid analysis (Φ3.9×150 mm, Waters)
Mobile phase: AccQ•Tag™ Eluent A/Acetonitrile=Gradient
Flow rate: 1 mL/min
Temperature: 37° C.
Injection volume: 10 μL
Detection: Fluorescence (250/395 nm)
Reference material for quantitative determination: Amino acid mixture standard, type H (Wako Pure Chemical Industries, Ltd.)

<<Test Group A: Synthesis of Polymer>>

Example A-1

Synthesis of PEG-PBLG-pAsp (DET) 10-35-5 Block Polymer (1) Synthesis of PEG-PBLG-PBLA 10-35-5 Block Polymer Under argon, to a reaction container were added 2 g (0.2 mmol) of polyethylene glycol having an aminopropyl group at one end (MeO-PEG10K-NH$_2$, average molecular weight: 10,000) and 25 mL of dehydrated dimethylsulfoxide (DMSO) to prepare a solution. 2.03 g (7.7 mmol) of β-benzyl-L-glutamateN-carboxylicanhydride (BLG-NCA, Mw=263.25) in a 38.5-fold amount with respect to the number of moles of MeO-PEG10K-NH$_2$ were added and the mixture was subjected to a reaction at 40° C. the whole day and night. After cooling down to room temperature, 0.3 g (1.2 mmol) of β-benzyl-L-aspartate N-carboxylic anhydride (BLA-NCA, Mw=249.22) in a 6-fold amount was added and the mixture was subjected to a reaction at 40° C. the whole day and night. After the reaction, the reaction mixture was suction-filtered with Kiriyama filter paper (Φ40 mm, 5B) using 20 mL of N,N-dimethylformamide (DMF) and the filtrate was added dropwise to 500 mL of a hexane/ethyl acetate (6/4) mixed solution for crystallization. The precipitated polymer was suction-filtered with Kiriyama filter paper (Φ60 mm, 5 C), 500 mL of a pure hexane/ethyl acetate (5/5) solution were further added, and the same washing operation was repeated twice. After that, drying under reduced pressure afforded a polymer powder. The resultant compound was confirmed as a target product by $^1$H-NMR and amino acid analysis. In a polymer (PEG-PBLG-PBLA) as an intermediate compound, the total number of benzyl esters is calculated based on an integral value of a PEG chain in the $^1$H-NMR spectrum. The polymerization degrees of PBLG and PBLA were calculated from the molar fractions of glutamic acid (Glu) and aspartic acid (Asp) in a polymer obtained by amino acid analysis. As a result, PBLG had a polymerization degree of 36 and PBLA had a polymerization degree of 5. The PEG-PBLG-PBLA Block polymer thus synthesized had a molecular weight of about 18,700 (3.53 g, 94% yield).

(2) Synthesis of PEG-PBLG-pAsp (DET) 10-35-5 Block Polymer

Under argon, to 1.5 g (0.080 mmol) of the PEG-PBLG-PBLA 10-35-5 Block polymer were added 15 mL of dehydrated DMF to prepare a solution. Under argon, to another reaction container were added 2.18 mL (20.1 mmol) of diethylenetriamine (DET) in a 50-fold amount (250 equivalent) with respect to PBLA. Each of the reaction solutions was cooled to 10° C. or less in an ice water bath. After the cooling, the polymer solution was added to the DET solution while rinsing with 5 mL of dehydrated DMF and the mixed solution was subjected to a reaction at 5° C. for 1 hour. To another container were added 6.7 mL (40.1 mmol) of 6 N hydrochloric acid in a 2-fold amount with respect to DET and the solution was preliminarily cooled at −20° C. After the reaction, the reaction solution was added to the hydrochloric acid solution which had been cooled to −20° C. while the reaction solution was cooled in an ice water bath, so that the temperature did not exceed 10° C. The resultant solution was then transferred to a dialysis membrane (MWCO: 3,500) and subjected to dialysis against 3 L of 0.01 N hydrochloric acid at 5° C. for 1 day (external solution exchange was performed twice) and further dialysis against 3 L of water at 5° C. for 1 day (external solution exchange was performed five times) (all external solutions for dialysis were preliminarily cooled to 5° C.). The dialyzed solution was treated with a filter (Nihon Millipore K.K., Sterivex™ GP 0.22 μm) and then lyophilized to afford a polymer powder. The resultant compound was confirmed as a target product by $^1$H-NMR and amino acid analysis. When both of PBLG and PBLA as amino acid benzyl ester derivatives are present in a polymer structure like a polymer (PEG-PBLG-PBLA) as an intermediate compound, an ester-amide exchange reaction occurs preferentially for PBLA in a reaction of such polymer with diethylenetriamine (DET) as an amine compound, and as a result, a DET group is introduced into an aspartic acid side chain. In the polymer PEG-PBLG-pAsp (DET), the number of benzyl esters of PBLG, which corresponds to the polymerization degree of PBLG, in the polymer is calculated based on the $^1$H-NMR spectrum. The polymerization degree of pAsp (DET) was calculated from the molar fractions of glutamic acid (Glu) and aspartic acid (Asp) in the polymer obtained by amino acid analysis. As a result, PBLG had a polymerization degree of 36 and pAsp (DET) had a polymerization degree of 5. The PEG-PBLG-pAsp (DET) 10-35-5 Block polymer thus synthesized had a molecular weight of about 19,000 (1.4 g, 92% yield).

Example A-2

Synthesis of PEG-PBLG-pAsp (DET) 10-25-5 Block Polymer

A polymer powder was obtained in the same manner as in Example A-1 except for: using 1.45 g (5.5 mmol) of BLG-NCA and 0.3 g (1.2 mmol) of BLA-NCA in 27.5- and 6-fold amounts, respectively, with respect to a number of moles of 2 g (0.2 mmol) of MeO-PEG10K-NH$_2$; and using diethyl ether as the poor solvent for first crystallization. The resultant compound was confirmed as a target product by $^1$H-NMR and amino acid analysis in the same manner as in Example A-1. As a result, PBLG had a polymerization degree of 24 and pAsp (DET) had a polymerization degree of 5. The PEG- PBLG-pAsp (DET) 10-25-5 Block polymer thus synthesized had a molecular weight of about 16,800 (1.43 g, 94% yield).

Example A-3

Synthesis of PEG-PBLG-pAsp (DET) 10-20-10 Block Polymer

A polymer powder was obtained in the same manner as in Example A-1 except for: using 1.16 g (4.4 mmol) of BLG-NCA and 0.6 g (2.4 mmol) of BLA-NCA in 22- and 12-fold amounts, respectively, with respect to a number of moles of 2 g (0.2 mmol) of MeO-PEG10K-NH$_2$; and using diethyl ether as the poor solvent for first crystallization. The resultant compound was confirmed as a target product by $^1$H-NMR and amino acid analysis in the same manner as in Example A-1. As a result, PBLG had a polymerization degree of 19 and pAsp (DET) had a polymerization degree of 11. The PEG-PBLG-pAsp (DET) 10-20-10 Block polymer thus synthesized had a molecular weight of about 17,100 (1.41 g, 90% yield).

Example A-4

Synthesis of PEG-PBLG-pAsp (DET) 10-35-5 Random Polymer

A polymer powder was obtained in the same manner as in Example A-1 except for: simultaneously adding 2.03 g (7.7 mmol) of BLG-NCA and 0.3 g (1.2 mmol) of BLA-NCA in 38.5- and 6-fold amounts, respectively, with respect to a numbers of moles of 2 g (0.2 mmol) of MeO-PEG10K-NH$_2$; and subjecting the mixture to a reaction at 40° C. the whole day and night. The resultant compound was confirmed as a target product by $^1$H-NMR and amino acid analysis in the same manner as in Example A-1. As a result, PBLG had a polymerization degree of 36 and pAsp (DET) had a polymerization degree of 5. The PEG-PBLG-pAsp (DET) 10-35-5 Random polymer thus synthesized had a molecular weight of about 19,000 (1.4 g, 92% yield).

Example A-5

Synthesis of PEG-PBLG-pAsp (DET) 10-25-5 Random Polymer

A polymer powder was obtained in the same manner as in Example A-4 except for using 1.45 g (5.5 mmol) of BLG-NCA and 0.3 g (1.2 mmol) of BLA-NCA in 27.5- and 6-fold amounts, respectively, with respect to a number of moles of 2 g (0.2 mmol) of MeO-PEG10K-NH$_2$. The resultant compound was confirmed as a target product by $^1$H-NMR and amino acid analysis in the same manner as in Example A-1. As a result, PBLG had a polymerization degree of 26 and pAsp (DET) had a polymerization degree of 5. The PEG-PBLG-pAsp (DET) 10-25-5 Random polymer thus synthesized had a molecular weight of about 16,800 (1.37 g, 90% yield).

Example A-6

Synthesis of PEG-PBLG-pAsp (DET) 10-20-10 Random Polymer

A polymer powder was obtained in the same manner as in Example A-4 except for using 1.16 g (4.4 mmol) of BLG-NCA and 0.6 g (2.4 mmol) of BLA-NCA in 22- and 12-fold amounts, respectively, with respect to a number of moles of 2 g (0.2 mmol) of MeO-PEG10K-NH$_2$. The resultant compound was confirmed as a target product by $^1$H-NMR and amino acid analysis in the same manner as in Example A-1. As a result, PBLG had a polymerization degree of 18 and pAsp (DET) had a polymerization degree of 10. The PEG-PBLG-pAsp (DET) 10-20-10 Random polymer thus synthesized had a molecular weight of about 17,100 (1.42 g, 91% yield).

Example A-7

Synthesis of PBLG-pAsp (DET) 35-5 Block Polymer (1) Synthesis of PBLG-PBLA 35-5 Block Polymer
Under argon, 40 μL (0.40 mmol) of n-butylamine were added to 15 mL of dehydrated DMSO to prepare a solution. 4.1 g (15.6 mmol) of BLG-NCA in a 38.5-fold amount with respect to a number of moles of a n-butylamine were added and the mixture was subjected to a reaction at 40° C. the whole day and night. After cooling down to room temperature, 0.61 g (2.43 mmol) of BLA-NCA in a 6-fold amount was added and the mixture was subjected to a reaction at 40° C. the whole day and night. After the reaction, the reaction mixture was suction-filtered with Kiriyama filter paper (Φ40 mm, 5B) using 20 mL of DMF and the filtrate was added dropwise to 1 L of diethyl ether for crystallization. The precipitated polymer was suction-filtered with Kiriyama filter paper (Φ60 mm, 5B), 1 L of a pure hexane/ethyl acetate (8/2) solution was further added, and the same washing operation was repeated twice. After that, drying under reduced pressure afforded a polymer powder (PBLG-PBLA 35-5 Block polymer).
(2) Synthesis of PBLG-pAsp (DET) 35-5 Block Polymer
A polymer powder was obtained in the same manner as in Example A-1 except for: using 1.5 g (0.171 mmol) of the PBLG-PBLA 35-5 Block polymer and a dialysis membrane (MWCO: 1,000); and performing no filter treatment after dialysis purification. The resultant compound was confirmed as a target product by $^1$H-NMR and amino acid analysis in the same manner as in Example A-1. As a result, PBLG had a polymerization degree of 35 and pAsp (DET) had a polymerization degree of 6. The PBLG-pAsp (DET) 35-5 Block polymer thus synthesized had a molecular weight of about 9,110 (1.22 g, 78% yield).

Example A-8

Synthesis of PBLG-pAsp (DET) 30-10 Block Polymer

A polymer powder was obtained in the same manner as in Example A-7 except for using 3.52 g (13.4 mmol) of BLG-NCA and 1.21 g (4.9 mmol) of BLA-NCA in 33- and 12-fold amounts, respectively, with respect to a number of moles of 40 μL (0.41 mmol) of n-butylamine. The resultant compound was confirmed as a target product by $^1$H-NMR and amino acid analysis in the same manner as in Example A-1. As a result, PBLG had a polymerization degree of 29 and pAsp (DET) had a polymerization degree of 12. The PBLG-pAsp (DET) 30-10 Block polymer thus synthesized had a molecular weight of about 9,380 (1.19 g, 74% yield).

Example A-9

Synthesis of PBLG-pAsp (DET) 25-5 Block Polymer

A polymer powder was obtained in the same manner as in Example A-7 except for using 3.66 g (13.9 mmol) of BLG- NCA and 0.76 g (3.0 mmol) of BLA-NCA in 27.5- and 6-fold amounts, respectively, with respect to a number of moles of 50 μL (0.51 mmol) of n-butylamine. The resultant compound was confirmed as a target product by $^1$H-NMR and amino acid analysis in the same manner as in Example A-1. As a result, PBLG had a polymerization degree of 25 and pAsp (DET) had a polymerization degree of 6. The PBLG-pAsp (DET) 25-5 Block polymer thus synthesized had a molecular weight of about 6,920 (1.23 g, 78% yield).

Example A-10

Synthesis of PBLG-pAsp (DET) 20-10 Block Polymer

A polymer powder was obtained in the same manner as in Example A-7 except for using 2.93 g (11.1 mmol) of BLG-NCA and 1.51 g (6.1 mmol) of BLA-NCA in 22- and 12-fold amounts, respectively, with respect to a number of moles of 50 μL (0.51 mmol) of n-butylamine. The resultant compound was confirmed as a target product by $^1$H-NMR and amino acid analysis in the same manner as in Example A-1. As a result, PBLG had a polymerization degree of 19 and pAsp (DET) had a polymerization degree of 10. The PBLG-pAsp (DET) 20-10 Block polymer thus synthesized had a molecular weight of about 7,190 (1.26 g, 76% yield).

Example A-11

Synthesis of PBLG-pAsp (DET) 35-5 Random Polymer

A polymer powder was obtained in the same manner as in Example A-7 except for: simultaneously adding 4.1 g (15.6 mmol) of BLG-NCA and 0.61 g (2.43 mmol) of BLA-NCA in 38.5- and 6-fold amounts, respectively, with respect to a number of moles of 40 μL (0.41 mmol) of n-butylamine; and subjecting the mixture to a reaction at 40° C. the whole day and night. The resultant compound was confirmed as a target product by $^1$H-NMR and amino acid analysis in the same manner as in Example A-1. As a result, PBLG had a polymerization degree of 34 and pAsp (DET) had a polymerization degree of 5. The PBLG-pAsp (DET) 35-5 Random polymer thus synthesized had a molecular weight of about 9,110 (1.26 g, 81% yield).

Example A-12

Synthesis of PBLG-pAsp (DET) 30-10 Random Polymer

A polymer powder was obtained in the same manner as in Example A-11 except for using 3.52 g (13.4 mmol) of BLG-NCA and 1.21 g (4.9 mmol) of BLA-NCA in 33- and 12-fold amounts, respectively, with respect to a number of moles of 40 μL (0.41 mmol) of n-butylamine. The resultant compound was confirmed as a target product by $^1$H-NMR and amino acid analysis in the same manner as in Example A-1. As a result, PBLG had a polymerization degree of 28 and pAsp (DET) had a polymerization degree of 10. The PBLG-pAsp (DET) 30-10 Random polymer thus synthesized had a molecular weight of about 9,380 (1.08 g, 67% yield).

Example A-13

Synthesis of PBLG-pAsp (DET) 25-5 Random Polymer

A polymer powder was obtained in the same manner as in Example A-11 except for using 3.66 g (13.9 mmol) of BLG-NCA and 0.76 g (3.0 mmol) of BLA-NCA in 27.5- and 6-fold amounts, respectively, with respect to a number of moles of 50 (0.51 mmol) of n-butylamine. The resultant compound was confirmed as a target product by $^1$H-NMR and amino acid analysis in the same manner as in Example A-1. As a result, PBLG had a polymerization degree of 26 and pAsp (DET) had a polymerization degree of 5. The PBLG-pAsp (DET) 25-5 Random polymer thus synthesized had a molecular weight of about 6,920 (1.08 g, 68% yield).

Example A-14

Synthesis of PBLG-pAsp (DET) 20-10 Random Polymer

A polymer powder was obtained in the same manner as in Example A-11 except for using 2.93 g (11.1 mmol) of BLG-NCA and 1.51 g (6.1 mmol) of BLA-NCA in 22- and 12-fold amounts, respectively, with respect to a number of moles of 50 (0.51 mmol) of n-butylamine. The resultant compound was confirmed as a target product by $^1$H-NMR and amino acid analysis in the same manner as in Example A-1. As a result, PBLG had a polymerization degree of 20 and pAsp (DET) had a polymerization degree of 11. The PBLG-pAsp (DET) 20-10 Random polymer thus synthesized had a molecular weight of about 7,190 (1.11 g, 67% yield).

Example A-15

Synthesis of PEG-PBLG-pAsp (DET) 10-20-15 Block Polymer

A polymer powder was obtained in the same manner as in Example A-1 except for: using 1.16 g (4.4 mmol) of BLG-NCA and 0.9 g (3.6 mmol) of BLA-NCA in 22- and 18-fold amounts, respectively, with respect to a number of moles of 2 g (0.2 mmol) of MeO-PEG10K-NH$_2$; using 2.79 mL (25.7 mmol) of diethylenetriamine (DET) in a 20-fold amount (300 equivalent) with respect to PBLA; and using 8.6 mL (51.4 mmol) of 6 N hydrochloric acid in a 2-fold amount with respect to DET. The resultant compound was confirmed as a target product by $^1$H-NMR and amino acid analysis in the same manner as in Example A-1. As a result, PBLG had a polymerization degree of 20 and pAsp (DET) had a polymerization degree of 17. The PEG-PBLG-pAsp (DET) 10-20-15 Block polymer thus synthesized had a molecular weight of about 18,500 (1.44 g, 91% yield).

Example A-16

Synthesis of PEG-PBLG-pAsp (DET) 10-20-20 Block Polymer

A polymer powder was obtained in the same manner as in Example A-1 except for: using 1.16 g (4.4 mmol) of BLG-NCA and 1.2 g (4.8 mmol) of BLA-NCA in 22- and 24-fold amounts, respectively, with respect to a number of moles of 2 g (0.2 mmol) of MeO-PEG10K-NH$_2$; using 3.52 mL (32.4 mmol) of diethylenetriamine (DET) in a 20-fold amount (400 equivalent) with respect to PBLA; and using 10.8 mL (64.9 mmol) of 6 N hydrochloric acid in a 2-fold amount with respect to DET. The resultant compound was confirmed as a target product by $^1$H-NMR and amino acid analysis in the same manner as in Example A-1. As a result, PBLG had a polymerization degree of 20 and pAsp (DET) had a polymerization degree of 20. The PEG-PBLG-pAsp (DET) 10-20-20

Example A-17

Synthesis of PEG-PBLG-pAsp (DET) 10-20-15 Random Polymer

A polymer powder was obtained in the same manner as in Example A-4 except for: using 1.16 g (4.4 mmol) of BLG-NCA and 0.9 g (3.6 mmol) of BLA-NCA in 22- and 18-fold amounts, respectively, with respect to a number of moles of 2 g (0.2 mmol) of MeO-PEG10K-$NH_2$; using 2.79 mL (25.7 mmol) of diethylenetriamine (DET) in a 20-fold amount (300 equivalent) with respect to PBLA; and using 8.6 mL (51.4 mmol) of 6 N hydrochloric acid in a 2-fold amount with respect to DET. The resultant compound was confirmed as a target product by $^1$H-NMR and amino acid analysis in the same manner as in Example A-1. As a result, PBLG had a polymerization degree of 20 and pAsp (DET) had a polymerization degree of 17. The PEG-PBLG-pAsp (DET) 10-20-15 Random polymer thus synthesized had a molecular weight of about 18,500 (1.39 g, 87% yield).

Example A-18

Synthesis of PEG-PBLG-pAsp (DET) 10-20-20 Random Polymer

A polymer powder was obtained in the same manner as in Example A-9 except for: using 1.16 g (4.4 mmol) of BLG-NCA and 1.2 g (4.8 mmol) of BLA-NCA in 22- and 24-fold amounts, respectively, with respect to a number of moles of 2 g (0.2 mmol) of MeO-PEG10K-$NH_2$; using 3.52 mL (32.4 mmol) of diethylenetriamine (DET) in a 20-fold amount (400 equivalent) with respect to PBLA; and using 10.8 mL (64.9 mmol) of 6 N hydrochloric acid in a 2-fold amount with respect to DET. The resultant compound was confirmed as a target product by $^1$H-NMR and amino acid analysis in the same manner as in Example A-1. As a result, PBLG had a polymerization degree of 19 and pAsp (DET) had a polymerization degree of 21. The PEG-PBLG-pAsp (DET) 10-20-20 Random polymer thus synthesized had a molecular weight of about 19,900 (1.46 g, 91% yield).

Example A-19

Synthesis of PBLG-pAsp (DET) 20-20 Block Polymer

A polymer powder was obtained in the same manner as in Example A-7 except for: using 2.34 g (8.9 mmol) of BLG-NCA and 2.42 g (9.7 mmol) of BLA-NCA in 22- and 24-fold amounts, respectively, with respect to a number of moles of 40 μL (0.41 mmol) of n-butylamine; using 7.61 mL (70.1 mmol) of diethylenetriamine (DET) in a 20-fold amount (400 equivalent) with respect to PBLA; and using 23.4 mL (140.2 mmol) of 6 N hydrochloric acid in a 2-fold amount with respect to DET. The resultant compound was confirmed as a target product by $^1$H-NMR and amino acid analysis in the same manner as in Example A-1. As a result, PBLG had a polymerization degree of 19 and pAsp (DET) had a polymerization degree of 20. The PBLG-pAsp (DET) 20-20 Block polymer thus synthesized had a molecular weight of about 9,920 (1.48 g, 85% yield).

Example A-20

Synthesis of PBLG-pAsp (DET) 20-15 Random Polymer

A polymer powder was obtained in the same manner as in Example A-11 except for: using 2.34 g (8.9 mmol) of BLG-NCA and 1.82 g (7.3 mmol) of BLA-NCA in 22- and 18-fold amounts, respectively, with respect to a number of moles of 40 μL (0.41 mmol) of n-butylamine; using 6.48 mL (59.7 mmol) of diethylenetriamine (DET) in a 20-fold amount (300 equivalent) with respect to PBLA; and using 19.9 mL (119.4 mmol) of 6 N hydrochloric acid in a 2-fold amount with respect to DET. The resultant compound was confirmed as a target product by $^1$H-NMR and amino acid analysis in the same manner as in Example A-1. As a result, PBLG had a polymerization degree of 19 and pAsp (DET) had a polymerization degree of 15. The PBLG-pAsp (DET) 20-15 Random polymer thus synthesized had a molecular weight of about 8,560 (1.51 g, 89% yield).

Example A-21

Synthesis of PBLG-pAsp (DET) 20-20 Random Polymer

A polymer powder was obtained in the same manner as in Example A-21 except for: using 2.34 g (8.9 mmol) of BLG-NCA and 2.42 g (9.7 mmol) of BLA-NCA in 22- and 24-fold amounts, respectively, with respect to a number of moles of 40 μL (0.41 mmol) of n-butylamine; using 7.61 mL (70.1 mmol) of diethylenetriamine (DET) in a 20-fold amount (400 equivalent) with respect to PBLA; and using 23.4 mL (140.2 mmol) of 6 N hydrochloric acid in a 2-fold amount of with respect to DET. The resultant compound was confirmed as a target product by $^1$H-NMR and amino acid analysis in the same manner as in Example A-1. As a result, PBLG had a polymerization degree of 19 and pAsp (DET) had a polymerization degree of 22. The PBLG-pAsp (DET) 20-20 Random polymer thus synthesized had a molecular weight of about 9,920 (1.42 g, 82% yield).

Reference Example A-1

Synthesis of PEG-PBLG-Ac 10-40

Under argon, to 18 g (1.8 mmol) of polyethylene glycol having an aminopropyl group at one end (MeO-PEG10K-$NH_2$, average molecular weight: 10,000) were added 200 mL of dehydrated N,N-dimethylformamide (DMF) to prepare a solution. 19.89 g (75.6 mmol) of BLG-NCA in a 42-fold amount with respect to a number of moles of MeO-PEG10K-$NH_2$ were added and the mixture was subjected to a reaction at 40° C. the whole day and night. To the reaction solution were added 1.7 mL (18 mmol) of acetic anhydride in a 10-fold amount with respect to a number of moles of MeO-PEG10K-$NH_2$ and the mixture was further subjected to a reaction at 40° C. for 6 hours. After the reaction, the reaction mixture was suction-filtered with Kiriyama filter paper (Φ60 mm, 5B) using 20 mL of N,N-dimethylformamide (DMF) and the filtrate was added dropwise to 2.5 L of a hexane/ethyl acetate (1/1) mixed solution for crystallization. The precipitated polymer was suction-filtered with Kiriyama filter paper (Φ95 mm, 5B) and the same washing operation was further repeated twice with 2.5 L of a pure hexane/ethyl acetate (1/1) solution. After that, drying under reduced pressure afforded a polymer powder. The resultant compound was confirmed as a target product by $^1$H-NMR in the same manner as in Example A-1. As a result, PBLG had a polymerization degree of 40. The PEG-PBLG-Ac 10-40 thus synthesized had a molecular weight of about 18,800 (33.18 g, 98% yield).

Comparative Example A-1

Synthesis of Long-Chain Type PEG-pAsp (DET ST 20%)

(1) Synthesis of Stearyl-NHS

Under argon, 3 g (10.55 mmol) of stearic acid, 1.456 g (12.65 mmol) of N-hydroxysuccinic acid imide in a 1.2-fold amount with respect to stearic acid, 2.426 g (12.65 mmol) of 1-ethyl-3-(3-dimethylaminopropyl)carbodiimide hydrochloride (EDC) in a 1.2-fold amount with respect to stearic acid, and 40 mL of dehydrated chloroform were added to prepare a solution and the solution was subjected to a reaction at room temperature the whole day and night. After the reaction, chloroform was removed with an evaporator and the residue was dissolved in diethyl ether. Extraction was performed with a separating funnel together with distilled water and divided several times, the aqueous layer was removed, and the diethyl ether layer was then collected. To the collected diethyl ether layer was added anhydrous magnesium sulfate and the whole was stirred for about 30 minutes and then suction-filtered with Kiriyama filter paper (Φ40 mm, 5B). Diethyl ether was removed from the filtrate with an evaporator and the residue was dissolved in 30 mL of chloroform. The resultant solution was added dropwise to 300 mL of EtOH for crystallization and then suction-filtered. The resultant was then stirred with 300 mL of EtOH for about 10 minutes, then suction-filtered with Kiriyama filter paper (Φ40 mm, 5B), and dried under reduced pressure to collect crystals. The resultant compound was confirmed as a target product by $^1$H-NMR (CDCl$_3$-d, T=20° C.). The active esterification rate, which was calculated based on the peak attributed to stearic acid (R—CH$_2$—COOH: 2.4 ppm) and the peak attributed to Stearyl-NHS (R—CH$_2$—NHS: 2.6 ppm), was 86%. The addition amount of the compound used for a reaction was calculated from the active esterification rate and the compound was added in an amount 1.16 times as much as the intended addition amount. Stearyl-NHS thus synthesized had a molecular weight of about 381.55 (1.9 g, 47% yield).

(2) Synthesis of PEG-PBLA 10-100

Under argon, to 1 g (0.1 mmol) of PEG10K-NH$_2$ were added 15 mL of dehydrated dichloromethane (CH$_2$Cl$_2$) to prepare a solution. Under argon, to another container were added 2.74 g (11 mmol) of BLA-NCA in a 110-fold amount with respect to a number of moles of PEG10K-NH$_2$, 6 mL of dehydrated DMF, and 30 mL of dehydrated CH$_2$Cl$_2$ to prepare a solution. The PEG10K-NH$_2$ solution was added to the BLA-NCA solution while rinsing with 15 mL of dehydrated CH$_2$Cl$_2$ (finally CH$_2$Cl$_2$/DMF=10/1) and the mixed solution was subjected to a reaction at 35° C. for 2 days. After the reaction, a polymer powder was obtained in the same manner as in Example A-1. The resultant compound was confirmed as a target product by $^1$H-NMR (DMSO-d$_6$, T=60° C.) (2.73 g, 90% yield).

(3) Synthesis of PEG-pAsp (DET) 10-100

Under argon, to 1.21 g (0.0397 mmol) of PEG-PBLA 10-100 were added 50 mL of dehydrated N-methyl-2-pyrrolidone (NMP) to prepare a solution. Under argon, to another reaction container were added 21.5 mL (198.4 mmol) of diethylenetriamine (DET) in a 50-fold amount with respect to a number of moles of PBLA and 10 mL of dehydrated NMP. A polymer powder was obtained in the same manner as in Example A-1 except for the operations. The resultant compound was confirmed as a target product by $^1$H-NMR (D$_2$O, T=70° C.) (1.0 g, 68% yield).

(4) Synthesis of PEG-pAsp (DET ST 20%) 10-100

Under argon, to 400 mg (0.0107 mmol) of PEG-pAsp (DET) 10-100 were added 15 mL of methanol and 1.49 mL (10.72 mmol) of triethylamine (TEA) in a 10-fold amount with respect to a number of moles of DET to prepare a solution. Under argon, to another container were added 95.1 mg (0.214 mmol) of Stearyl-NHS in a 0.2-fold amount with respect to a number of moles of aspartic acid and the mixture was dissolved with 5 mL of CH$_2$Cl$_2$. Each of the solutions was cooled in an ice water bath. The Stearyl-NHS solution was added to the polymer solution while rinsing with 10 mL of CH$_2$Cl$_2$ (finally: 15 mL of MeOH/15 mL of CH$_2$Cl$_2$) and the mixed solution was subjected to a reaction at 5° C. the whole day and night. After the reaction, the reaction mixture was added dropwise to 270 mL of diethyl ether for crystallization. A centrifugation operation (2,380 G, 10 min, 4° C.) was carried out to collect a polymer. Washing by the same centrifugation operation was repeated twice with 90 mL of pure diethyl ether to remove the supernatant. The residue was then dissolved in 40 mL of a 50% MeOH aqueous solution, transferred to a dialysis membrane (MWCO: 3,500), and subjected to dialysis against 3 L of 0.01 N hydrochloric acid at 5° C. for 1 day (external solution exchange was performed twice) and further dialysis against 3 L of water at 5° C. for 1 day (external solution exchange was performed twice) (all external solutions for dialysis were preliminarily cooled to 5° C.). The dialyzed solution was treated with a filter (Nihon Millipore K. K., Sterivex™ GP 0.22 μm) and then lyophilized to afford a polymer powder. The resultant compound was confirmed as a target product by $^1$H-NMR (D$_2$O, T=70° C.). As a result, pAsp (DET) had a polymerization degree of 99 and the stearoyl (ST) group introduction rate was 21%. PEG-pAsp (DET ST 20%) 10-100 thus synthesized had a molecular weight of about 42,700 (432 mg, 95% yield).

Comparative Example A-2

Synthesis of Long-Chain Type pAsp (DET ST 20%)

(1) Synthesis of PBLA 100

Under argon, to 2.77 g (11.13 mmol) of BLA-NCA in a 110-fold amount with respect to n-butylamine were added 4 mL of dehydrated DMF and 30 mL of dehydrated CH$_2$Cl$_2$ to prepare a solution. Under argon, to another container were added 10 μL (0.101 mmol) of n-butylamine and 1 mL of CH$_2$Cl$_2$. The n-butylamine solution was added to the BLA-NCA solution while rinsing with 9 mL of dehydrated CH$_2$Cl$_2$ (finally CH$_2$Cl$_2$/DMF=10/1) and the mixed solution was subjected to a reaction at 35° C. for 2 days. After the reaction, a polymer powder was obtained in the same manner as in Example A-1. The resultant compound was confirmed as a target product by $^1$H-NMR (DMSO-d$_6$, T=60° C.) (1.78 g, 86% yield).

(2) Synthesis of pAsp (DET) 100

Under argon, a polymer powder was obtained in the same manner as in Comparative Example A-1 except that 1.2 g (0.0585 mmol) of PBLA 100 were used in place of PEG-PBLA 10-100. The resultant compound was confirmed as a target product by $^1$H-NMR (D$_2$O, T=70° C.) (1.29 g, 81% yield).

(3) Synthesis of pAsp (DET ST 20%) 100

Under argon, a polymer powder was obtained in the same manner as in Comparative Example A-1 except that 400 mg (0.0147 mmol) of pAsp (DET) 100 were used in place of PEG-pAsp (DET) 10-100. The resultant compound was confirmed as a target product by $^1$H-NMR (D$_2$O, T=70° C.). The stearoyl (ST) group introduction rate was 21%. pAsp (DET ST 20%) 100 thus synthesized had a molecular weight of about 32,700 (471 mg, 98% yield).

<<Test Group B: Preparation of Polymer Particle Composition>>

Examples B-1 to B-10 and B-18 to B-24 and Comparative Examples B-1 and B-2

To 30 mg each of the polymers described in Tables 1 and 2 were added 2 mL of a 10 mM HEPES buffer (pH 7.4) and the mixtures were stirred at 4° C. for 1 hour to prepare suspensions. The suspensions were subjected to ultrasonication (130 W, 1-second pulse, 5 minutes) to afford Polymer particle compositions 1 to 10, 18 to 24, and C1 and C2 each containing a polymer component at a polymer concentration of 15 mg/mL.

Examples B-11 to B-14

To 40 mg each of the polymers described in Table 1 were added 2 mL of dimethylsulfoxide to prepare solutions. The solutions were transferred to a dialysis membrane (MWCO: 3,500) and subjected to dialysis using 500 mL of a 10 mM HEPES buffer (pH 7.4) as an external solution at room temperature for 2 hours. After that, external solution exchange was performed and dialysis was carried out at 5° C. for 12 hours, and external solution exchange was then performed once again and dialysis was carried out at 5° C. for 2 hours. The dialyzed solutions were collected and the total amount of each of the solutions was adjusted to 5.3 mL with a 10 mM HEPES buffer (pH 7.4) to afford Polymer particle compositions 11 to 14 each containing a polymer component at a polymer concentration of 15 mg/mL.

Examples B-15 to B-17

To 20 mg each of the polymers described in Table 1 were added 2 mL of acetone and 2 mL of methanol to prepare solutions. A solvent was evaporated by blowing nitrogen gas over the solutions, followed by drying under reduced pressure with a vacuum pump for 6 hours. To each of the resultant polymer films were added 2.7 mL of a 10 mM HEPES buffer (pH 7.4) and the mixtures were stirred at 4° C. for 1 hour to prepare suspensions. The suspensions were subjected to ultrasonication (130 W, 1-second pulse, 5 minutes) to afford Polymer particle compositions 15 to 17 each containing a polymer component at a polymer concentration of 15 mg/mL.

<Evaluation on Particle Diameter of Polymer Particle Composition>

To 50 µL each of Polymer particle compositions 1 to 24 and C1 and C2 obtained above were added 700 µL of a 10 mM HEPES buffer (pH:7.4) to prepare samples. Those samples were measured for their cumulant average particle diameters by a dynamic light scattering method using a light scattering particle diameter measurement apparatus (Malvern Instruments, Zetasizer Nano ZS). Tables 1 and 2 show the results.

TABLE 1

| Example | Polymer particle composition | Polymer | Amount used (mg) | Average particle diameter (nm) |
|---|---|---|---|---|
| B1 | 1 | PEG-PBLG-pAsp (DET) 10-35-5 Block polymer: (Example A-1) | 30 | 49 |
| B2 | 2 | PEG-PBLG-pAsp (DET) 10-25-5 Block polymer: (Example A-2) | 30 | 46 |
| B3 | 3 | PEG-PBLG-pAsp (DET) 10-20-10 Block polymer: (Example A-3) | 30 | 34 |
| B4 | 4 | PEG-PBLG-pAsp (DET) 10-35-5 Random polymer: (Example A-4) | 30 | 56 |
| B5 | 5 | PEG-PBLG-pAsp (DET) 10-25-5 Random polymer: (Example A-5) | 30 | 50 |
| B6 | 6 | PEG-PBLG-pAsp (DET) 10-20-10 Random polymer: (Example A-6) | 30 | 28 |
| B7 | 7 | PBLG-pAsp (DET) 30-10 Block polymer: (Example A-8) | 30 | 112 |
| B8 | 8 | PBLG-pAsp (DET) 20-10 Block polymer: (Example A-10) | 30 | 103 |
| B9 | 9 | PBLG-pAsp (DET) 30-10 Random polymer: (Example A-12) | 30 | 109 |
| B10 | 10 | PBLG-pAsp (DET) 20-10 Random polymer: (Example A-14) | 30 | 77 |
| B11 | 11 | PBLG-pAsp (DET) 35-5 Block polymer: (Example A-7) PEG-PBLG 10-40: (Reference Example A-1) | 40 40 | 114 |
| B12 | 12 | PBLG-pAsp (DET) 30-10 Block polymer: (Example A-8) PEG-PBLG 10-40: (Reference Example A-1) | 40 40 | 89 |
| B13 | 13 | PBLG-pAsp (DET) 25-5 Block polymer: (Example A-9) PEG-PBLG 10-40: (Reference Example A-1) | 40 40 | 92 |
| B14 | 14 | PBLG-pAsp (DET) 20-10 Block polymer: (Example A-10) PEG-PBLG 10-40: (Reference Example A-1) | 40 40 | 99 |
| B15 | 15 | PBLG-pAsp (DET) 25-5 Block polymer: (Example A-9) PEG-PBLG 10-40: (Reference Example A-1) | 20 20 | 66 |
| B16 | 16 | PBLG-pAsp (DET) 30-10 Random polymer: (Example A-12) PEG-PBLG 10-40: (Reference Example A-1) | 20 20 | 54 |
| B17 | 17 | PBLG-pAsp (DET) 25-5 Random polymer: (Example A-13) PEG-PBLG 10-40: (Reference Example A-1) | 20 20 | 57 |
| Comparative Example | | | | |
| B1 | C1 | PEG-pASP (DET ST 20%) 10-100: (Comparative Example A-1) | 30 | 57 |
| B2 | C2 | pASP (DET ST 20%) 100: (Comparative Example A-2) | 30 | 54 |

TABLE 2

| Example | Polymer particle composition | Polymer | Amount used (mg) | Average particle diameter (nm) |
|---|---|---|---|---|
| B18 | 18 | PEG-PBLG-pAsp (DET) 10-20-15 Block polymer: (Example A-15) | 30 | 35 |
| B19 | 19 | PEG-PBLG-pAsp (DET) 10-20-20 Block polymer: (Example A-16) | 30 | 35 |
| B20 | 20 | PEG-PBLG-pAsp (DET) 10-20-15 Random polymer: (Example A-17) | 30 | 31 |

TABLE 2-continued

| Example | Polymer particle composition position | Polymer | Amount used (mg) | Average particle diameter (nm) |
|---|---|---|---|---|
| B21 | 21 | PEG-PBLG-pAsp (DET) 10-20-20 Random polymer: (Example A-18) | 30 | 19 |
| B22 | 22 | PBLG-pAsp (DET) 20-20 Block polymer: (Example A-19) | 30 | 70 |
| B23 | 23 | PBLG-pAsp (DET) 20-15 Random polymer: (Example A-20) | 30 | 87 |
| B24 | 24 | PBLG-pAsp (DET) 20-20 Random polymer: (Example A-21) | 30 | 37 |

<<Test Group C: Preparation of Complex>>

The following siRNAs were used for the preparation of complexes described later. Those siRNAs are available from Nippon EGT Co., Ltd.

(1) siRNA (Luc): siRNA that is designed using a Vargula luciferase gene as a target and has a double strand formed by a conventional method using 5'-CUUACGCUGAGUACU-UCGAdTdT-3' (SEQ ID NO: 1) as a sense strand and using 5'-UCGAAGUACUCAGCGUAAGdTdT-3' (SEQ ID NO: 2) as an antisense strand.

(2) siRNA (Plk1): siRNA that is designed using a human Polo-like kinase 1 (Plk1) gene as a target and has a double strand formed by a conventional method using 5'-CCA-UUAACGAGCUGCUUAAdTdT-3' (SEQ ID NO: 3) as a sense strand and using 5'-UUAAGCAGCUCGUUAAUG-GdTdT-3' (SEQ ID NO: 4) as an antisense strand. The Plk1 gene is an important kinase in the M phase of cell division. When the siRNA (Plk1) is introduced into cells, the siRNA (Plk1) induces apoptosis.

Example C-1

Polymer Particle Composition Encapsulating siRNA (Luc)

siRNA (Luc) was dissolved in a 10 mM HEPES buffer (pH 7.4) to prepare an 80 μM siRNA solution. To 12.5 μL of the siRNA solution were added and mixed 87.5 μL each of Polymer particle compositions 1 to 24 and C1 and C2 having concentrations adjusted so that the N/P ratio was 16 and the mixtures were then left to stand still at 4° C. for 2 hours to encapsulate siRNA into polymer particles. This afforded Polymer particle compositions 1 to 24 and C1 and C2 each encapsulating siRNA (Luc) as polymer-siRNA complexes. The "N/P ratio" as used herein means [Concentration of amino group in polyamino acid side chain in polymer contained in polymer particle composition]/[Concentration of phosphate group in nucleic acid].

<Evaluation on Particle Diameter>

To 70 μL each of Polymer particle compositions 1 to 24 and C1 and C2 each encapsulating siRNA (Luc) obtained above were added 630 μL of a 10 mM HEPES buffer (pH 7.4) to prepare samples each containing 1 μM siRNA. The samples were measured for their cumulant average particle diameters by a dynamic light scattering method using a light scattering particle diameter measurement apparatus (Malvern Instruments, Zetasizer Nano ZS). Tables 3 and 4 show the results.

TABLE 3

| | Polymer particle composition encapsulating siRNA (Luc) | | | | | |
|---|---|---|---|---|---|---|
| | 1 | 2 | 3 | 4 | 5 | 6 |
| Average particle diameter (nm) | 49 | 46 | 34 | 56 | 50 | 33 |
| | 7 | 8 | 9 | 10 | 11 | 12 |
| Average particle diameter (nm) | 114 | 106 | 127 | 80 | 149 | 92 |
| | 13 | 14 | 15 | 16 | 17 | C1 | C2 |
| Average particle diameter (nm) | 124 | 112 | 69 | 74 | 63 | 69 | 157 |

TABLE 4

| | Polymer particle composition encapsulating siRNA (Luc) | | | | | |
|---|---|---|---|---|---|---|
| | 18 | 19 | 20 | 21 | 22 | 23 | 24 |
| Average particle diameter (nm) | 33 | 32 | 32 | 31 | 91 | 103 | 137 |

<Evaluation on siRNA Release Rate>

To 5 μL (siRNA concentration: 10 μM) each of Polymer particle compositions 1 to 6, 11 to 24, and C1 and C2 each encapsulating siRNA (Luc) obtained above were added 90 μL of fetal bovine serum (FBS) and 5 μL of 0.5 M EDTA, and the mixture was left to stand still at 37° C. for 24 hours (FBS treatment). As a control, the same treatment was carried out except that 95 μL of a 10 mM HEPES buffer (pH 7.4) were used in place of FBS and 0.5 M EDTA (control treatment).

The release rate of siRNA in each composition after the FBS treatment or control treatment was analyzed by an electrophoresis method as described below. Each composition containing 100 ng of siRNA was loaded to a polyacrylamide gel (Novex 20% TBE Gel, Invitrogen), and electrophoresis was carried out using a TBE solution as an electrophoresis buffer under conditions of an applied voltage of 100 V and an electrophoresis time of 1 hour. After the electrophoresis, the gel was stained with ethidium bromide, and a gel image was captured on a UV transilluminator. After that, the band intensity was analyzed with image analysis software (Image J, NIH) to quantitatively determine the siRNA release rate. Tables 5 and 6 show the results of quantitative determination of the siRNA release rate. The siRNA release rate of each composition was calculated from a relative value of the band intensity when the band intensity evaluated for siRNA alone was defined as 100%.

Figure 2:
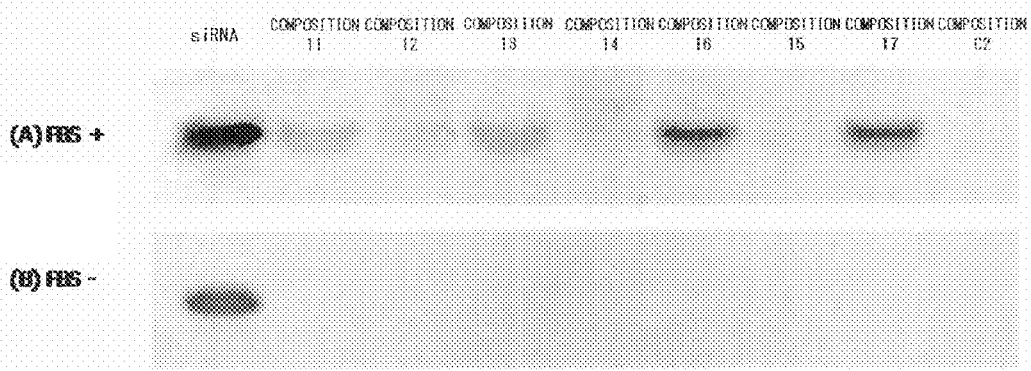
FIG. 2 show gel images after electrophoresis of polymer particle compositions each encapsulating siRNA (Luc).

Further, FIG. 1 show gel images after the electrophoresis obtained for Polymer particle compositions 1 to 6 and C1 each encapsulating siRNA (Luc) and FIG. 2 show gel images after the electrophoresis obtained for Polymer particle compositions 11 to 17 and C2 each encapsulating siRNA (Luc). In FIGS. 1 and 2, the image (A) means the results of the samples subjected to the FBS treatment and the image (B) means the results of the samples subjected to the control treatment.

TABLE 5

| Polymer particle composition encapsulating siRNA (Luc) | Cationic polymer | siRNA release rate (%) |
|---|---|---|
| 1 | PEG-PBLG-pAsp (DET) 10-35-5 Block polymer | 4.5 |

TABLE 5-continued

| Polymer particle composition encapsulating siRNA (Luc) | Cationic polymer | siRNA release rate (%) |
|---|---|---|
| 2 | PEG-PBLG-pAsp (DET) 10-25-5 Block polymer | 9.3 |
| 3 | PEG-PBLG-pAsp (DET) 10-20-10 Block polymer | 10.7 |
| 18 | PEG-PBLG-pAsp (DET) 10-20-15 Block polymer | 8.8 |
| 19 | PEG-PBLG-pAsp (DET) 10-20-20 Block polymer | 10.8 |
| 4 | PEG-PBLG-pAsp (DET) 10-35-5 Random polymer | 75.5 |
| 5 | PEG-PBLG-pAsp (DET) 10-25-5 Random polymer | 82.1 |
| 6 | PEG-PBLG-pAsp (DET) 10-20-10 Random polymer | 72.3 |
| 20 | PEG-PBLG-pAsp (DET) 10-20-15 Random polymer | 77.1 |
| 21 | PEG-PBLG-pAsp (DET) 10-20-20 Random polymer | 88.0 |
| C1 | PEG-pAsp (DET-ST 20%) 10-100 | 1.1 |

As shown in Table 5, each composition formed of a short-chain type polymer base material having a PEG chain had an siRNA release rate of 4% or more. In addition, each composition of Examples formed of a random type polymer base material having a cationic polyamino acid chain segment had an siRNA release rate of 70% or more. Further, each composition of Examples formed of a block type polymer base material having a cationic polyamino acid chain segment had an siRNA release rate reduced to 15% or less. As understood from this fact, the block type polymer base material can retain residual siRNA in the base material for later release and is more suitable for a long-term sustained release type base material than the random type polymer base material.

TABLE 6

| Polymer particle composition encapsulating siRNA (Luc) | Cationic polymer | siRNA release rate (%) |
|---|---|---|
| 11 | PBLG-pAsp (DET) 35-5 Block polymer | 17.0 |
| 12 | PBLG-pAsp (DET) 30-10 Block polymer | 12.8 |
| 13 | PBLG-pAsp (DET) 25-5 Block polymer | 26.1 |
| 14 | PBLG-pAsp (DET) 20-10 Block polymer | 9.26 |
| 15 | PBLG-pAsp (DET) 25-5 Block polymer | 4.64 |
| 22 | PBLG-pAsp (DET) 20-20 Block polymer | 3.3 |
| 16 | PBLG-pAsp (DET) 30-10 Random polymer | 47.9 |
| 17 | PBLG-pAsp (DET) 25-5 Random polymer | 45.7 |
| 23 | PBLG-pAsp (DET) 20-15 Random polymer | 36.3 |
| 24 | PBLG-pAsp (DET) 20-20 Random polymer | 53.1 |
| C2 | pAsp (DET-ST 20%) 100 | 1.3 |

As shown in Table 6, each composition formed of a short-chain type polymer base material free of a PEG chain also had an siRNA release rate of 3% or more. In addition, each composition of Examples formed of a random type polymer base material had an siRNA release rate of 35% or more. Further, each composition of Examples formed of a block type polymer base material had an siRNA release rate reduced to 30% or less. As understood from this fact, the block type polymer base material can retain residual siRNA in the base material for later release, and also in this case, is more suitable for a long-term sustained release type base material than the random type polymer base material regardless of the presence or absence of a PEG chain.

Example C-2

Polymer Particle Composition Encapsulating siRNA (Plk1)

Polymer particle compositions 7 to 10 and C2 each encapsulating siRNA (Plk1) were obtained in the same manner as in Example C-1 except for: using siRNA (Plk1) as the siRNA; and using Polymer particle compositions 7 to 10 and C2 having concentrations adjusted so that the N/P ratios were 4, 8, 16, and 32.

<Evaluation on Activity on MDA-MB-231 Cells>

A 10 mM HEPES buffer (pH 7.4) was added to each of Polymer particle compositions 7 to 10 and C2 each encapsulating siRNA (Plk1) obtained above so that the siRNA concentration was adjusted to 1 µM/ml. Human breast cancer-derived MDA-MB-231 cells were seeded in a 96-well dish at a ratio of 2,000 cells per well, and after 24 hours, each composition was added to the medium. Adjustment was made so that the final concentration of siRNA in the medium was 100 nM. After the culture for additional 96 hours, the cell survival rate was evaluated using a cell count measurement kit Cell Counting Kit-8 (DOJINDO LABORATORIES). The same experiment was carried out using siRNA (Luc) as an inactive control sequence.

As a result of the evaluation, remarkable decreases in cell count were observed in Polymer particle compositions 7 to 10 each encapsulating siRNA (Plk1) as compared to Polymer particle compositions 7 to 10 each encapsulating siRNA (Luc). Specifically, the cell survival rates (%) at N/P ratios of 4, 8, 16, and 32 were 48.2 (s.d.=1.1), 26.5 (s.d.=1.2), 12.4 (s.d.=1.6), and 6.7 (s.d.=0.8), respectively, in Polymer particle composition 7 encapsulating siRNA (Plk1), whereas the cell survival rates were 67.1 (s.d.=3.6), 45.5 (s.d.=1.9), 33.8 (s.d.=1.6), and 36.1 (s.d.=0.7), respectively, in Polymer particle composition 7 encapsulating siRNA (Luc). Further, the cell survival rates (%) at N/P ratios of 4, 8, 16, and 32 were 60.0 (s.d.=9.0), 23.2 (s.d.=5.0), 2.6 (s.d.=0.3), and 3.3 (s.d.=1.2), respectively, in Polymer particle composition 8 encapsulating siRNA (Plk1), whereas the cell survival rates were 88.3 (s.d.=2.2), 66.4 (s.d.=1.7), 24.9 (s.d.=1.8), and 29.4 (s.d.=1.5), respectively, in Polymer particle composition 8 encapsulating siRNA (Luc). Further, the cell survival rates (%) at N/P ratios of 8 and 16 were 48.8 (s.d.=8.5) and 0.9 (s.d.=1.5), respectively, in Polymer particle composition 9 encapsulating siRNA (Plk1), whereas the cell survival rates were 79.0 (s.d.=11.6) and 16.9 (s.d.=3.9), respectively, in Polymer particle composition 9 encapsulating siRNA (Luc). Further, the cell survival rate at an N/P ratio of 16 was 13.9 (s.d.=10.7) in Polymer particle composition 10 encapsulating siRNA (Plk1), whereas the cell survival rate was 52.8 (s.d.=3.9) in Polymer particle composition 10 encapsulating siRNA (Luc). Those results mean that Polymer particle compositions 7 to 10 each encapsulating siRNA (Plk1) functioned normally. In contrast, as illustrated in FIG. 3, there was no remarkable difference between siRNA (Plk1) encapsulation and siRNA (Luc) encapsulation in Polymer particle composition C2.

The invention claimed is:

1. A cationic polyamino acid capable of associating with a nucleic acid, the cationic polyamino acid comprising:
   1 to 20 units of one or more cationic amino acid residue(s) having a cationic group in a side chain; and
   a plurality of hydrophobic amino acid residues having a hydrophobic group in a side chain,
   wherein the cationic polyamino acid has the following formula (1):

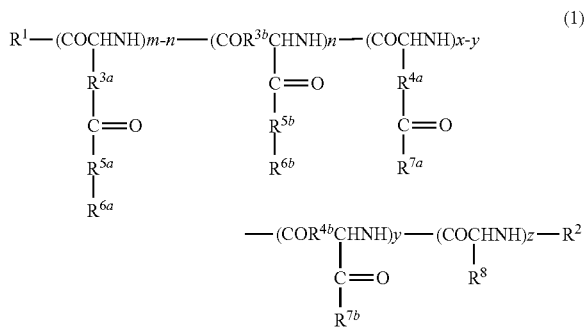

where: $R^1$ is a hydroxyl group or an unsubstituted or substituted linear or branched alkyloxy group having 1 to 12 carbon atoms, an unsubstituted or substituted linear or branched alkenyloxy group having 2 to 12 carbon atoms, an unsubstituted or substituted linear or branched alkynyloxy group having 2 to 12 carbon atoms, or an unsubstituted or substituted linear or branched alkyl-substituted imino group having 1 to 12 carbon atoms;

$R^2$ is a hydrogen atom, an unsubstituted or substituted linear or branched alkyl group having 1 to 12 carbon atoms, or an unsubstituted or substituted linear or branched alkylcarbonyl group having 1 to 24 carbon atoms;

$R^{3a}$, $R^{3b}$, $R^{4a}$, and $R^{4b}$ are each independently a methylene group or an ethylene group;

$R^{5a}$ and $R^{5b}$ are each independently —O— or —NH—;

$R^{6a}$ and $R^{6b}$ are each independently a saturated or unsaturated linear or branched aliphatic hydrocarbon group having 6 to 27 carbon atoms, an aromatic hydrocarbon group having 6 to 27 carbon atoms, or a sterol group derived from a sterol;

$R^{7a}$ and $R^{7b}$ are each independently selected from the group consisting of:
—NH—$(CH_2)_{p1}$—[NH—$(CH_2)_{q1}$—]$_{r1}$NH$_2$ (i);
—NH—$(CH_2)_{p2}$—N[—$(CH_2)_{q2}$—NH$_2$]$_2$ (ii);
—NH—$(CH_2)_{p3}$—N{[—$(CH_2)_{q3}$—NH$_2$][—$(CH_2)_{q4}$—NH—]$_{r2}$H} (iii); and
—NH—$(CH_2)_{p4}$—N{—$(CH_2)_{q5}$—N[—$(CH_2)_{q6}$—NH$_2$]$_2$}$_2$ (iv), where: p1 to p4, q1 to q6, and r1 and r2 are each independently an integer of 1 to 5;

$R^8$ is a side chain of an amino acid selected from the group consisting of lysine, ornithine, arginine, homoarginine, and histidine;

m is an integer of 5 to 80;
n is an integer of 0 to m;
x is an integer of 1 to 20;
y is an integer of 0 to x; and
z is an integer of 0 to 20,
with the proviso that:
1≤x+z≤20, repeating units having the groups $R^{6a}$, $R^{6b}$, $R^{7a}$, and $R^{7b}$ and $R^8$ may be bound to each other in any order, and each of $R^{6a}$, $R^{6b}$, $R^{7a}$, $R^{7b}$ and $R^8$ is arbitrarily selectable for each respective amino acid residue of the cationic polyamino acid.

2. The cationic polyamino acid according to claim 1, wherein the cationic polyamino acid is a block polymer including a segment formed of a plurality of the cationic amino acid residue(s) and a segment formed of a plurality of the hydrophobic amino acid residues.

3. A polymer particle composition comprising a plurality of the cationic polyamino acids according to claim 1 bound to each other.

4. A complex comprising the cationic polyamino acid according to claim 1 bound to a nucleic acid.

5. The complex according to claim 4, wherein the nucleic acid is siRNA.

6. The polymer particle composition according to claim 3, further comprising a nucleic acid encapsulated within the polymer particle composition.

7. The polymer particle composition according to claim 6, wherein the nucleic acid is siRNA.

8. A block copolymer capable of associating with a nucleic acid, the block copolymer comprising:
   1 to 20 units of one or more cationic amino acid residue(s) having a cationic group in a side chain; and
   a plurality of hydrophobic amino acid residues having a hydrophobic group in a side chain,
   wherein the block copolymer has the following formula (1):

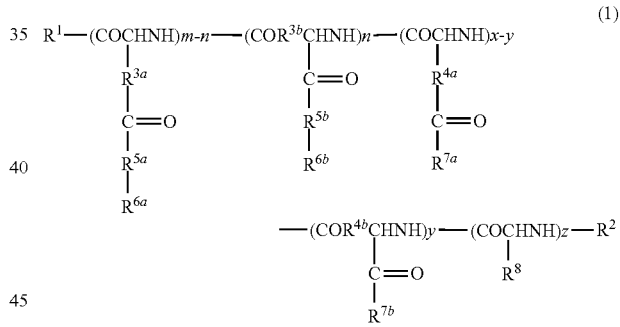

wherein: $R^1$ is a hydrophilic polymer chain segment;

$R^2$ is a hydrogen atom, an unsubstituted or substituted linear or branched alkyl group having 1 to 12 carbon atoms, or an unsubstituted or substituted linear or branched alkylcarbonyl group having 1 to 24 carbon atoms;

$R^{3a}$, $R^{3b}$, $R^{4a}$, and $R^{4b}$ are each independently a methylene group or an ethylene group;

$R^{5a}$ and $R^{5b}$ are each independently —O— or —NH—;

$R^{6a}$ and $R^{6b}$ are each independently a saturated or unsaturated linear or branched aliphatic hydrocarbon group having 6 to 27 carbon atoms, an aromatic hydrocarbon group having 6 to 27 carbon atoms, or a sterol group derived from a sterol;

$R^{7a}$ and $R^{7b}$ are each independently selected from the group consisting of:
—NH—$(CH_2)_{p1}$—[NH—$(CH_2)_{q1}$—]$_{r1}$NH$_2$ (i);
—NH—$(CH_2)_{p2}$—N[—$(CH_2)_{q2}$—NH$_2$]$_2$ (ii);
—NH—$(CH_2)_{p3}$—N{[—$(CH_2)_{q3}$—NH$_2$][—$(CH_2)_{q4}$—NH—]$_{r2}$H} (iii); and —NH—(CH$_2$)$_{p4}$—N{—(CH$_2$)$_{q5}$—N[—(CH$_2$)$_{q6}$—NH$_2$]$_2$}$_2$ (iv), wherein: p1 to p4, q1 to q6, and r1 and r2 are each independently an integer of 1 to 5;

R$^8$ is a side chain of an amino acid selected from the group consisting of lysine, ornithine, arginine, homoarginine, and histidine;

m is an integer of 5 to 80;

n is an integer of 0 to m;

x is an integer of 1 to 20;

y is an integer of 0 to x; and z is an integer of 0 to 20, with the proviso that:

1≤x+z≤20, repeating units having the groups R$^{6a}$, R$^{6b}$, R$^{7a}$, and R$^{7b}$ and R$^8$ may be bound to each other in any order, and each of R$^{6a}$, R$^{6b}$, R$^{7a}$, R$^{7b}$ and R$^8$ is arbitrarily selectable for each respective amino acid residue of the block copolymer acid.

9. The block copolymer according to claim 8, wherein R$^1$ is poly(ethylene glycol), polysaccharide, poly(vinylpyrrolidone), poly(vinyl alcohol), poly(acrylic amide), poly(acrylic acid), poly(methacrylic amide), poly(methacrylic acid), poly(methacrylic acid ester), poly(acrylic acid ester), polyamino acid, poly(malic acid), or a derivative thereof.

10. A polymer particle composition comprising a plurality of the block copolymers according to claim 8 bound to each other.

11. A complex comprising the block copolymer according to claim 8 bound to a nucleic acid.

12. The complex according to claim 11, wherein the nucleic acid is siRNA.

13. The polymer particle composition according to claim 10, further comprising a nucleic acid encapsulated within the polymer particle composition.

14. The polymer particle composition according to claim 13, wherein the nucleic acid is siRNA.

15. A block copolymer capable of associating with a nucleic acid, the block copolymer having a formula selected from the group consisting of the following formula (2) and formula (3):

wherein: R$^1$ is a hydroxyl group or an unsubstituted or substituted linear or branched alkyloxy group having 1 to 12 carbon atoms, an unsubstituted or substituted linear or branched alkenyloxy group having 2 to 12 carbon atoms, an unsubstituted or substituted linear or branched alkynyloxy group having 2 to 12 carbon atoms, or an unsubstituted or substituted linear or branched alkyl-substituted imino group having 1 to 12 carbon atoms;

R$^2$ is a hydrogen atom, an unsubstituted or substituted linear or branched alkyl group having 1 to 12 carbon atoms, or an unsubstituted or substituted linear or branched alkylcarbonyl group having 1 to 24 carbon atoms;

R$^{3a}$, R$^{3b}$, R$^{4a}$, and R$^{4b}$ are each independently a methylene group or an ethylene group;

R$^{5a}$ and R$^{5b}$ are each independently —O— or —NH—;

R$^{6a}$ and R$^{6b}$ are each independently a saturated or unsaturated linear or branched aliphatic hydrocarbon group having 6 to 27 carbon atoms, an aromatic hydrocarbon group having 6 to 27 carbon atoms, or a steryl group derived from a sterol;

R$^{7a}$ and R$^{7b}$ are each independently selected from the group consisting of:

—NH—(CH$_2$)$_{p1}$—[NH—(CH$_2$)$_{q1}$—]$_{r1}$NH$_2$ (i);

—NH—(CH$_2$)$_{p2}$—N[—(CH$_2$)$_{q2}$—NH$_2$]$_2$ (ii);

—NH—(CH$_2$)$_{p3}$—N{[—(CH$_2$)$_{q3}$—NH$_2$][—(CH$_2$)$_{q4}$—NH—]$_{r2}$H} (iii); and —NH—(CH$_2$)$_{p4}$—N{—(CH$_2$)$_{q5}$—N[—(CH$_2$)$_{q6}$—NH$_2$]$_2$}$_2$ (iv), wherein: p1 to p4, q1 to q6, and r1 and r2 are each independently an integer of 1 to 5;

R$^8$ is a side chain of an amino acid selected from the group consisting of lysine, ornithine, arginine, homoarginine, and histidine;

L$^1$ and L$^3$ are each independently —S—S— or a valence bond;

L$^2$ is —NH—, —O—, —O(CH$_2$)$_{p1}$—NH—, or —L$^{2a}$—(CH$_2$)$_{q1}$—L$^{2b}$—, wherein p1 and q1 are each independently an integer of 1 to 5, L$^{2a}$ is OCO, OCONH, NHCO, NHCOO, NHCONH, CONH, or COO, and L$^{2b}$ is NH or O;

L$^4$ is —OCO—(CH$_2$)$_{p2}$—CO—, —NHCO—(CH$_2$)$_{p3}$—CO—, or —L$^{4a}$—(CH$_2$)$_{q2}$—CO—, wherein p2, p3, and q2 are each independently an integer of 1 to 5 and L$^{4a}$ is OCONH, —CH$_2$NHCO—, NHCOO, NHCONH, CONH, or COO;

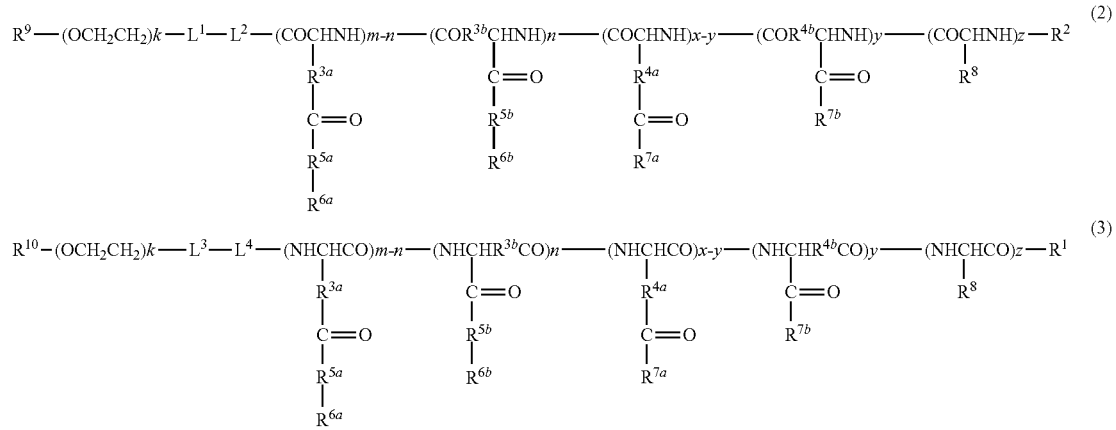

R$^9$ and R$^{10}$ are each independently a hydrogen atom or an unsubstituted or substituted linear or branched alkyl group having 1 to 12 carbon atoms;

k is an integer of 30 to 20,000;

m is an integer of 5 to 80;

n is an integer of 0 to m;

x is an integer of 1 to 20;
y is an integer of 0 to x; and
z is an integer of 0 to 20,
with the proviso that:
$1 \leq x+z \leq 20$,
repeating units having the groups $R^{6a}$, $R^{6b}$, $R^{7a}$, and $R^{7b}$ and $R^8$ may be bound to each other in any order, and each of $R^{6a}$, $R^{6b}$, $R^{7a}$, $R^{7b}$ and $R^8$ is arbitrarily selectable for each respective amino acid residue of the block copolymer acid.

16. A polymer particle composition comprising a plurality of the block copolymers according to claim 15 bound to each other.

17. A complex comprising the block copolymer according to claim 15 bound to a nucleic acid.

18. The complex according to claim 17, wherein the nucleic acid is siRNA.

19. The polymer particle composition according to claim 16, further comprising a nucleic acid encapsulated within the polymer particle composition.

20. The polymer particle composition according to claim 19, wherein the nucleic acid is siRNA.

21. A method of treating cancer, rheumatoid arthritis or retinitis, comprising:
intravenously administering to a patient in need thereof a therapeutically effective amount of the complex of claim 17.

22. A method of treating cancer, rheumatoid arthritis or retinitis, comprising:
intravenously administering to a patient in need thereof a therapeutically effective amount of the complex of claim 11.

23. A method of treating cancer, rheumatoid arthritis or retinitis, comprising:
intravenously administering to a patient in need thereof a therapeutically effective amount of the complex of claim 4.

* * * * *

UNITED STATES PATENT AND TRADEMARK OFFICE
CERTIFICATE OF CORRECTION

PATENT NO. : 8,853,167 B2  
APPLICATION NO. : 13/258663  
DATED : October 7, 2014  
INVENTOR(S) : Yasuki Kato et al.

Page 1 of 1

It is certified that error appears in the above-identified patent and that said Letters Patent is hereby corrected as shown below:

In the Claims

Column 33, line 46, replace "sterol group" with -- steryl group --

Column 34, line 60, replace "sterol group" with -- steryl group --

Signed and Sealed this  
Twenty-fourth Day of February, 2015

Michelle K. Lee  
*Deputy Director of the United States Patent and Trademark Office*

UNITED STATES PATENT AND TRADEMARK OFFICE
CERTIFICATE OF CORRECTION

| | |
|---|---|
| PATENT NO. | : 8,853,167 B2 |
| APPLICATION NO. | : 13/258663 |
| DATED | : October 7, 2014 |
| INVENTOR(S) | : Yasuki Kato et al. |

It is certified that error appears in the above-identified patent and that said Letters Patent is hereby corrected as shown below:

On the title page item (73), the following additional Assignee name should appear:

(73) Assignee: The University of Tokyo, Tokyo (JP)

Signed and Sealed this
Twenty-fifth Day of August, 2015

Michelle K. Lee
*Director of the United States Patent and Trademark Office*